(12) United States Patent
Gonzales et al.

(10) Patent No.: US 11,779,276 B2
(45) Date of Patent: Oct. 10, 2023

(54) SYSTEMS AND APPARATUSES FOR PROTECTING CONTINUOUS GLUCOSE MONITORING AND INSULIN INFUSION DEVICES

(71) Applicant: Freedom Band LLC, Fresno, CA (US)

(72) Inventors: Jesse R. Gonzales, Fresno, CA (US); Carrie K. Gonzales, Fresno, CA (US); Mark-Ryan H. Sewell, Eagle River, AK (US)

( * ) Notice: Subject to any disclaimer, the term of this patent is extended or adjusted under 35 U.S.C. 154(b) by 0 days.

(21) Appl. No.: 17/849,494

(22) Filed: Jun. 24, 2022

(65) Prior Publication Data

US 2023/0026387 A1 Jan. 26, 2023

Related U.S. Application Data

(60) Provisional application No. 63/223,620, filed on Jul. 20, 2021.

(51) Int. Cl.
*A61B 5/00* (2006.01)
*A61B 5/145* (2006.01)

(52) U.S. Cl.
CPC ........ *A61B 5/6833* (2013.01); *A61B 5/14532* (2013.01); *A61B 5/6831* (2013.01); *A61B 2560/0406* (2013.01)

(58) Field of Classification Search
CPC .............. A61B 5/14532; A61B 5/6831; A61B 2560/0406; A61B 5/14865; G04B 37/1486
See application file for complete search history.

(56) References Cited

U.S. PATENT DOCUMENTS

| D431,650 S | 10/2000 | Guala et al. |
| 6,631,282 B2 * | 10/2003 | Rule ............... A61B 5/6841 600/344 |
| 6,875,199 B2 | 4/2005 | Altman |

(Continued)

FOREIGN PATENT DOCUMENTS

| CA | 2667192 | 5/2008 |
| KR | 300946388.0000 | 2/2018 |

OTHER PUBLICATIONS

DiaStuff, facebook.com/Diastuff.de/ (Year: 2020).*

(Continued)

*Primary Examiner* — Eric F Winakur
*Assistant Examiner* — Abid A Mustansir
(74) *Attorney, Agent, or Firm* — Marcus N. DiBuduo; John R. Aaron

(57) ABSTRACT

Systems and apparatuses for securing and protecting diabetes management devices, such as continuous glucose monitoring (CGM) devices and insulin infusion sets. An apparatus comprises a base having multiple pairs of arms which can be attached to a band. The apparatus also comprises a shell for retaining a diabetes management device and which may be unitarily formed with, or removably attached to, the base. A system may include an apparatus, a diabetes management device retained in the shell of the apparatus, and a band attached to the base of the apparatus. The band may be placed around a body part of a user, such as an arm or the abdomen. A system can include an adhesive patch which can adhere to the shell of an apparatus and which has an adhesive layer overlaid with multiple liners having cutlines formed therebetween.

23 Claims, 27 Drawing Sheets

(56) References Cited

U.S. PATENT DOCUMENTS

| | | | |
|---|---|---|---|
| D540,942 S | 4/2007 | Homra et al. | |
| 7,736,310 B2 | 6/2010 | Taub | |
| D656,232 S | 3/2012 | Villasana | |
| D672,667 S * | 12/2012 | Mix | D10/70 |
| 8,640,707 B2 | 2/2014 | Rozier et al. | |
| D809,370 S | 2/2018 | Tang | |
| 10,357,191 B2 | 7/2019 | Di Resta | |
| D856,123 S | 8/2019 | Bancroft et al. | |
| D884,885 S | 5/2020 | Hu et al. | |
| D908,871 S | 1/2021 | Hu et al. | |
| D927,551 S | 8/2021 | Hudnall et al. | |
| D938,557 S | 12/2021 | Duncan et al. | |
| D940,203 S | 1/2022 | Hudnall et al. | |
| D942,248 S | 2/2022 | Laaksonen et al. | |
| D954,255 S | 6/2022 | Pontecorvo | |
| 2018/0042558 A1 | 2/2018 | Cabrera, Jr. et al. | |
| 2019/0167167 A1 | 6/2019 | Mitchell | |
| 2019/0231972 A1 | 8/2019 | Cash | |
| 2020/0323554 A1 | 10/2020 | Cash | |
| 2022/0288303 A1 | 9/2022 | Hollis et al. | |

OTHER PUBLICATIONS https://web.archive.org/web/20191206034743/https://en.wikipedia.org/wiki/File:Sparadrap_3.jpg; Dec. 6, 2019 (Year: 2019).*

International Search Report and Written Opinion relating to International application No. PCT/US2022/035184, dated Nov. 16, 2022.

Clixstorm DIY. "Shell Back Case & Applying The Patch System : Freedom Arm Band for Dexcom G6 & More!". YouTube. Published Nov. 12, 2020 (Retrieved Dec. 14, 2022 from: https://www.youtube.com/watch?v=nf55w0vRkgl).

Clixstorm DIY. "Protective CGM Bands for Dexcom Libre Omnipod & Medkonic!". YouTube. Published Nov. 26, 2020 (Retrieved Dec. 14, 2022 from https://www.youtube.com/watch?v=uArWCpsaGiQ).

Clixstorm DIY. "Putting the Dexcom G6 CGM Monitor on & How It Works 4 Diabetics T1D JDRF". YouTube. Published Jan. 26, 2021 (Retrieved Dec. 14, 2022 from https://www.youtube.com/watch?v=rjAUTMcpve8).

* cited by examiner

SYSTEMS AND APPARATUSES FOR PROTECTING CONTINUOUS GLUCOSE MONITORING AND INSULIN INFUSION DEVICES

CROSS-REFERENCE TO RELATED APPLICATIONS

The present application claims priority to, and the benefit of, U.S. Provisional Patent Application No. 63/223,620, filed Jul. 20, 2021, which is hereby incorporated by reference in its entirety.

FIELD OF THE INVENTION

The present invention concerns apparatuses and systems for protecting continuous glucose monitoring (CGM) devices and insulin infusion sets. More particularly, some embodiments of the present invention concern apparatuses which can be engaged with a CGM device or insulin pump to secure and protect it while being worn by a user. Additionally, some embodiments of the present invention concern systems comprising apparatuses, or components thereof, bands, and patches which may be used collectively to secure and protect CGM devices or insulin pumps.

BACKGROUND OF THE INVENTION

Management of diabetes generally consists of periodic blood sugar checks and insulin infusion, as needed. As part of this practice, continuous glucose monitoring (CGM) devices are commonly used to monitor a user's blood glucose levels in real-time and without the need to draw blood to be analyzed by a blood glucose sensor every time the user decides to check their blood glucose levels. As a result of the inherent advantages of CGM devices, such devices are commonly and widely used among diabetics. In addition, another device commonly worn by diabetics is an insulin pump which is used to administer insulin to a user's bloodstream in response to, or in anticipation of, rising blood glucose levels. Such devices are worn on a user's body—for example, on the user's upper arm or abdomen (though other application sites exist)—and are typically secured to the application area by conventional adhesive patches on the underside of the device.

Conventional securing means are often unreliable as they may have low durability and/or poor adhesive strength. Furthermore, conventional securing means are typically adapted only for particular conditions and uses, thus limiting the usability of the CGM device or insulin pump. Additionally, such conventional securing means may be prone to inadvertent removal caused by a device catching a foreign object and being pulled away from a user's skin or by repeated or prolonged activities, such as swimming, or any other activity which may cause perspiration or which may involve physical contact with objects and/or people (e.g., basketball).

Further to the above, conventional adhesive patches are commonly used to help secure CGM devices or insulin pumps to a user's skin. However, a drawback of such convention patches is that they are commonly constructed using allergenic materials (e.g., latex) which, for some users, may make it difficult to use the patch for prolonged periods or, in some cases, for any amount of time at all. Additionally, many devices are standardly equipped with a conventional patch which may be pre-applied to the side of the device which adheres to a user's skin which, if the user is allergic to any of the patch materials, may make it difficult for the user to wear the device.

Therefore, the need exists for an accessory or system to adequately secure and protect CGM devices and insulin infusion sets. In particular, the need exists for an accessory or system which can be used with existing CGM devices and insulin infusion sets and which can secure and protect the same during use. Additionally, the need exists for an accessory or system which may engaged with a CGM device or insulin pump to allow a user to wear the device or pump while performing a variety of activities without the CGM device or insulin pump becoming inadvertently removed from the user's body and, at the same time, preventing the accessory from being inadvertently disengaged from the CGM device or pump. Furthermore, the need exists for a hypoallergenic adhesive patch which can be used with existing CGM devices or insulin pumps.

BRIEF SUMMARY OF THE INVENTION

The present invention generally concerns systems and apparatuses for protecting and securing CGM devices (including sensors), insulin infusion sets, and insulin pumps (collectively hereafter referred to, generally, as "diabetes management device"). According to some embodiments of the present invention, an apparatus may comprise a shell for positioning a diabetes management device therein and a base for securing the apparatus to a user. In some embodiments, a diabetes management device may have a side wall around its perimeter, a top wall, and a bottom wall. In some aspects, the shell and the base may be unitarily formed or, according to other aspects, may be removably attached. In some embodiments, the shell may include a retention opening generally formed in a center of the shell. The retention opening may, according to some embodiments, have a shape which may be similar to a shape of a bottom wall of a diabetes management device.

In accordance with some embodiments of the present invention, the shell may include a retention wall which may have an inner surface which may have a shape similar to a shape of a side wall of a diabetes management device. According to some aspects, the retention wall may extend from a top side or a bottom side of the shell or, according to other aspects, the retention wall may define the width of the shell such that it does not extend beyond either side of the shell. In some embodiments, the retention wall may comprise one or more ridges disposed on an inner surface of the retention wall which may be configured to abut a diabetes management device when retained in the shell. According to some embodiments of the present invention, a shell may comprise one or more grooves for receiving a corresponding tab of a base. In some aspects, a groove be formed in an outer surface of the retention wall.

According to some embodiments, the retention wall may comprise a lip extending along a portion, or the entirety, of the inner surface of the retention wall. In some aspects, the lip may protrude in a direction away from a top side or a bottom side of the shell and may, in some embodiments, be oriented toward the retention opening (when viewed from the top side or bottom side of the shell). In some embodiments, an inner surface of the lip may be rounded and may contour an edge of a diabetes management device retained within the shell.

In some embodiments, a shell may include an enclosure wall adjacent to the retention wall. An enclosure wall may, according to some embodiments, may be at a top edge of the retention wall. In some embodiments, the enclosure wall may extend radially inward from the retention wall. In some aspects, the enclosure wall may be rounded so as to contour a diabetes management device when retained in the shell. More particularly, and according to some embodiments, the enclosure wall may have an inner surface which may have a shape similar to a shape of a top wall of a diabetes management device. In some embodiments, the enclosure wall may partially enclose one side of the retention opening to form an enclosure opening. In some aspects, the enclosure opening which may be centrally aligned with the retention opening. In other embodiments, the enclosure wall may fully enclose one side of the retention opening, such that the enclosure wall lacks an opening and the retention opening may only be visible on a side of the shell opposite to the enclosure wall.

In accordance with some embodiments, a shell may comprise an adhesion wall which may be configured to be engaged with an adhesive. More particularly, and according to some aspects, a bottom surface of the adhesion wall (i.e., the surface oriented toward a user's skin when the shell is being worn by the user) may be configured to adhere to an adhesive. Likewise, a top surface of the adhesion wall (i.e., the surface oriented away from a user's skin when the shell is being worn by the user) may be configured to adhere to an adhesive. In some embodiments, an adhesion wall may comprise a plurality of holes formed into various shapes.

According to some embodiments of the present invention, the base of an apparatus may comprise a base opening configured to receive a shell of the apparatus. According to some aspects, the base opening may have a shape similar to a shape of an outer surface of the retention wall of the shell. In some embodiments, the base may comprise a base wall having an inner surface defining the perimeter of the base opening. According to some aspects, one or more tabs may be formed on the inner surface of the base wall and may be configured to be received in one or more corresponding grooves of a retention wall of a shell. In some embodiments, a top or a bottom surface of the base may comprise at least one indicator (e.g., an arrow) corresponding to at least one tab which may provide an indication of the position of the tab.

In accordance with some embodiments of the present invention, the base of an apparatus may comprise at least one pair of arms disposed at a lateral side of the base with each arm having an exposed end. In some embodiments, a pair of arms may be generally oriented such that the longitudinal axes of each are coaxial. In particular, a pair of arms may be oriented such that an end of a first arm is adjacent to an end of a second arm. According to some aspects, an end of an arm may be generally disposed near a medial point of a lateral side of the base. In other aspects, an end of an arm may be generally disposed near a distal end of a lateral side of the base. In some embodiments, an arm may comprise one or more notches disposed at or near an end of the arm. According to some aspects, a notch may be disposed on an inner surface (i.e., the surface oriented toward a center of the base) of an arm.

In some embodiments, an end of an arm may comprise at least two noncoplanar surfaces. In some aspects, a proximal surface of an end of a first arm (i.e., the surface nearest a center of the base) may be about parallel to a proximal surface of an end of a second arm. Likewise, and according to some embodiments, a distal surface of an end of a first arm (i.e., the surface furthest from a center of the base) may be about parallel to a distal surface of an end of a second arm. In other aspects, a proximal surface of an end of a first arm may be about parallel to a distal surface of an end of a second arm (and vice versa).

In accordance with some embodiments of the present invention, a base may comprise one or more band apertures which may be configured to receive and release a band. In some embodiments, an aperture may be generally defined by an opening between the ends of a pair of adjacent arms. A base, according to some embodiments, may comprise one or more band slots which may be configured to receive a portion of a band. According to some aspects, a band slot may be elongated and generally parallel to a lateral edge of the base. In some embodiments, a band slot may be generally defined by an opening between the base wall and a pair of arms. With reference to the above, and according to some aspects, a band may be received within the band slot, via an adjacent band aperture, and may be retained therein. The band may also be released from the band slot via the band aperture.

According to some implementations of the present invention, an apparatus may be used as part of a system for protecting and securing a diabetes management device. In general, a system may include an apparatus, in accordance with some embodiments of the present invention, and a band engaged with the apparatus, with the diabetes management device being retained within the shell of the apparatus. More particularly, and according to some implementations, a portion of a band may be positioned around each of a first pair of arms and a second pair of arms of a base of the apparatus, with a first end of the band retained in a first band slot and a second end of the band retained in a second band slot. In some implementations, the ends of the band may be retained in band slots on opposing lateral sides of the base of the apparatus.

According to some embodiments of the present invention, system for protecting a diabetes management device may further include an adhesive patch. According to some aspects, patch may comprise a patch opening, an adhesive layer, a plurality of liners overlaying the adhesive layer, and a plurality of cutlines formed between the liners. In some embodiments of the present invention, an adhesive patch may comprise a bottom side (oriented toward a user's skin when being worn) and a top side (oriented away from a user's skin when being worn), with the bottom side being overlaid with one or more liners. In some embodiments, an adhesive patch may comprise a plurality of liners with a plurality of cuts formed between adjacent liners.

In some embodiments, an adhesive patch may comprise an opening through which a portion of a shell may be disposed. According to some aspects, an opening in an adhesive patch may have a shape similar to a shape of an outer surface of the retention wall of a shell (which may have a diabetes management device retained therein) for positioning the retention wall therein. In some embodiments, disposed underneath a liner on a bottom side of an adhesive patch may be an adhesive layer which may be adapted to adhere to a user's skin and/or a shell. In particular, and in accordance with some embodiments, a portion of the adhesive layer may be adapted to adhere to a user's skin and another portion of the adhesive layer may be adapted to adhere to a portion of a shell. More particularly, a portion of the adhesive layer may be adapted to adhere to the adhesion wall of a shell.

In some implementations, an adhesive patch may be adhered to a user's skin and the shell of the apparatus, with a diabetes management device retained within the shell. In some aspects, the patch may be positioned above a top surface of the adhesion wall of the shell and with the retention wall of the shell positioned within the base opening of a base. The base of the apparatus, which may be removable from the shell, may be engaged with the shell such that the inner surface of the base wall (or tab thereof) abuts the outer surface of the retention wall of the shell. Alternatively, and in accordance with embodiments previously described herein, the base of the apparatus may be engaged with the shell such that one or more tabs of the base are received within one or more corresponding grooves of the shell. When the base is engaged with the shell, a bottom surface of the base (i.e., the surface oriented toward a user's skin when being worn) may contact a surface of the top side of the adhesive patch. Furthermore, and in accordance with embodiments previously described herein, a band may be attached to the base (via, e.g., the band slots of the base).

DETAILED DESCRIPTION OF THE INVENTION

The invention, in its various aspects, will be explained in greater detail below. While the invention will be described in conjunction with several exemplary embodiments, the exemplary embodiments themselves do not limit the scope of the invention. Similarly, the exemplary illustrations in the accompanying drawings, where like elements have like numerals, do not limit the scope of the exemplary embodiments and/or invention, including any length, angles, or other measurements provided. Rather the invention, as defined by the claims, may cover alternatives, modifications, and/or equivalents of the exemplary embodiments.

Figure 9:
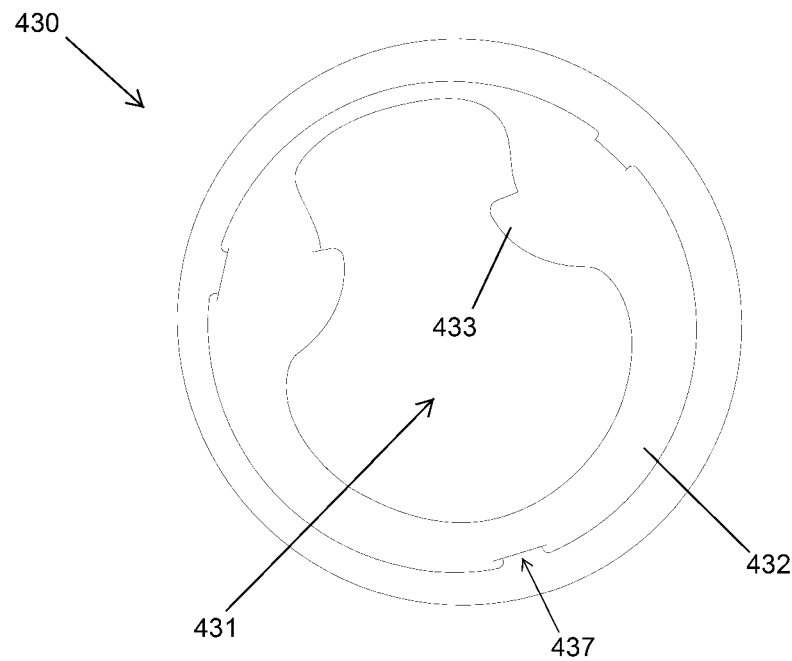
FIG. 9 is a bottom view diagram illustrating an exemplary shell of an apparatus for use with a diabetes management device, in accordance with some embodiments of the present invention.
Figure 10:
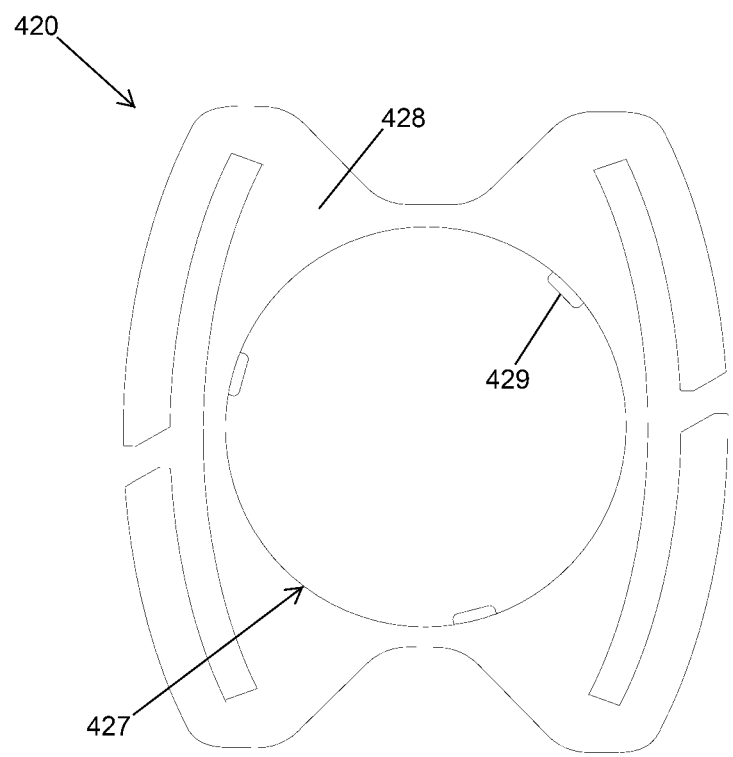
FIG. 10 is a top (bottom) view diagram illustrating an exemplary base of an apparatus for use with a diabetes management device, in accordance with some embodiments of the present invention.

With reference, generally to FIGS. 1-4, and in accordance with some embodiments of the present invention, an apparatus 10 for securing and protecting a diabetes management device may generally comprise a base 20 and a shell 30, which may be unitarily formed. It is to be appreciated, however, that, according to other embodiments, a base and a shell may be separately formed (see, e.g., FIGS. 9 and 10). According to some embodiments, a base and/or a shell may be constructed from rigid or flexible material. As illustrated more clearly in FIGS. 1 and 3, base 20 may be generalized as the lateral portions of apparatus 10, whereas shell 30 may be generalized as the central portion of apparatus 10 generally encircled by base 20. Shell 30 may comprise a shell opening 31 disposed, generally, in a center of shell 30 (and therefore apparatus 10). As more clearly illustrated in FIG. 3, shell opening 31 may comprise a shape that is generally that of an oval (as viewed in the orientation illustrated in FIG. 3) which may be about the same shape as the diabetes management device for which apparatus 10 is configured. It is to be appreciated, however, that the shell opening may comprise any shape and size so as to accommodate other types of diabetes management devices (as shown, for example, in the other exemplary embodiments of FIGS. 21-38).

Figure 1:
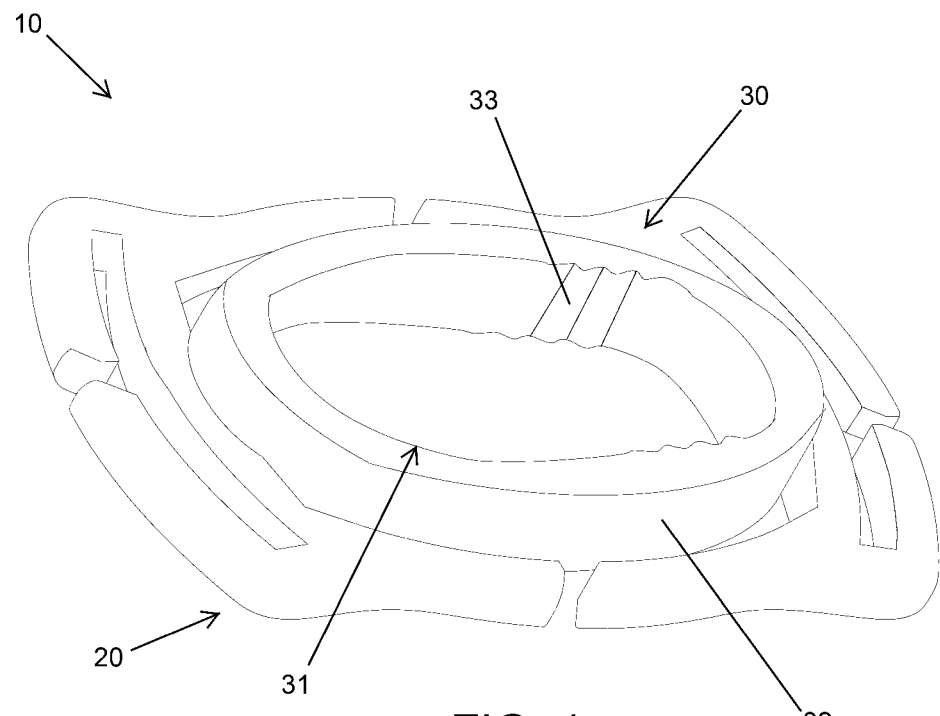
FIG. 1 is a perspective view diagram illustrating an exemplary apparatus for use with a diabetes management device, in accordance with some embodiments of the present invention.
Figure 2:
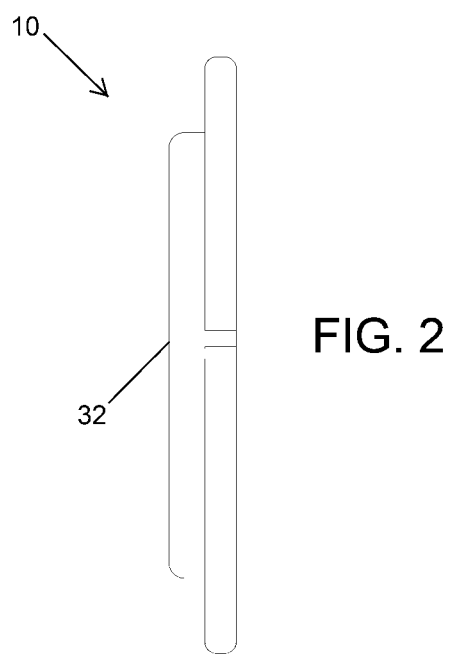
FIG. 2 is a side view diagram illustrating the apparatus of FIG. 1, in accordance with some embodiments of the present invention.
Figure 3:
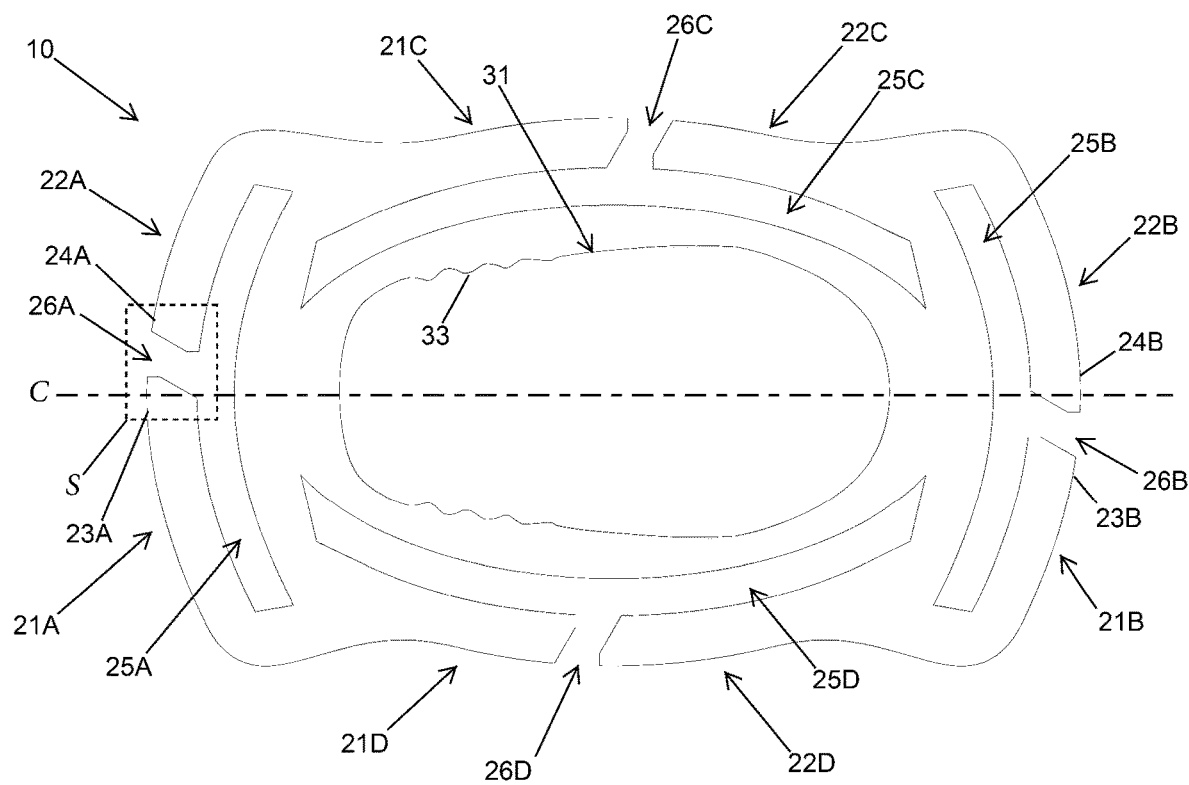
FIG. 3 is a top (bottom) view diagram illustrating the apparatus of FIG. 1, in accordance with some embodiments of the present invention.

As further illustrated in FIG. 1, and according to some embodiments, shell 30 may comprise a retention wall 32 which generally defines a perimeter of shell opening 31. On a top side of apparatus 10 (i.e., the side facing away from a user's skin when wearing apparatus 10), retention wall 32 may extend or protrude, generally, above the adjacent surface of base 20, as more clearly illustrated in FIGS. 1 and 2. As illustrated in FIGS. 1 and 3, retention wall 32 may comprise a plurality of ridges 33 disposed on an inner surface of retention wall 32. According to some embodiments, ridges 33 (or the like) may be configured to abut an outer surface of a diabetes management device when the diabetes management device is retained within shell 30.

In some embodiments of the present invention, a shell may comprise a lip (or the like) which may extend from a retention wall. For example, referring, briefly to FIGS. 9 and 11, a retention wall 432 of a shell 430 may comprise a lip 433 extending from a portion of a retention wall 432. In some embodiments, and as more clearly illustrated in FIG. 11, an inner surface of lip 433 may be coplanar with an inner surface of retention wall 432. Furthermore, and according to some embodiments, a protruding edge of lip 433 may be oriented toward a center of a shell opening 431 of shell 430 which may limit or prevent any displacement of a diabetes management device which may be retained within shell 430. An inner surface of lip 433 may also be rounded according a shape of a lateral edge of a diabetes management device such that lip 433 may contour the lateral edges of a diabetes management device (or portions thereof) which may be retained within shell 430, thereby further limiting or preventing displacement of the diabetes management device.

Figure 5:
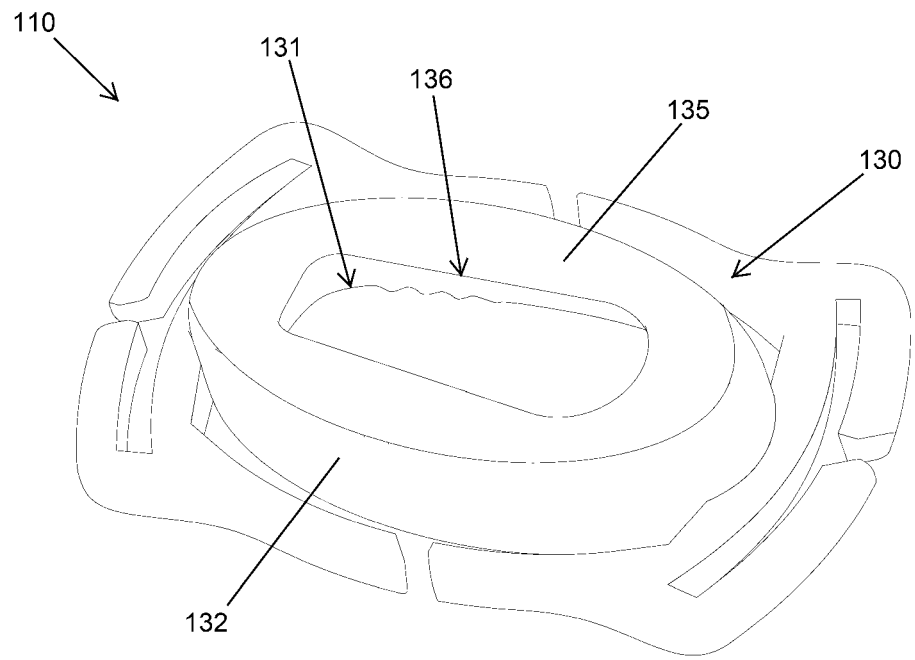
FIG. 5 is a perspective view diagram illustrating an exemplary apparatus for use with a diabetes management device, in accordance with some embodiments of the present invention.
Figure 6:
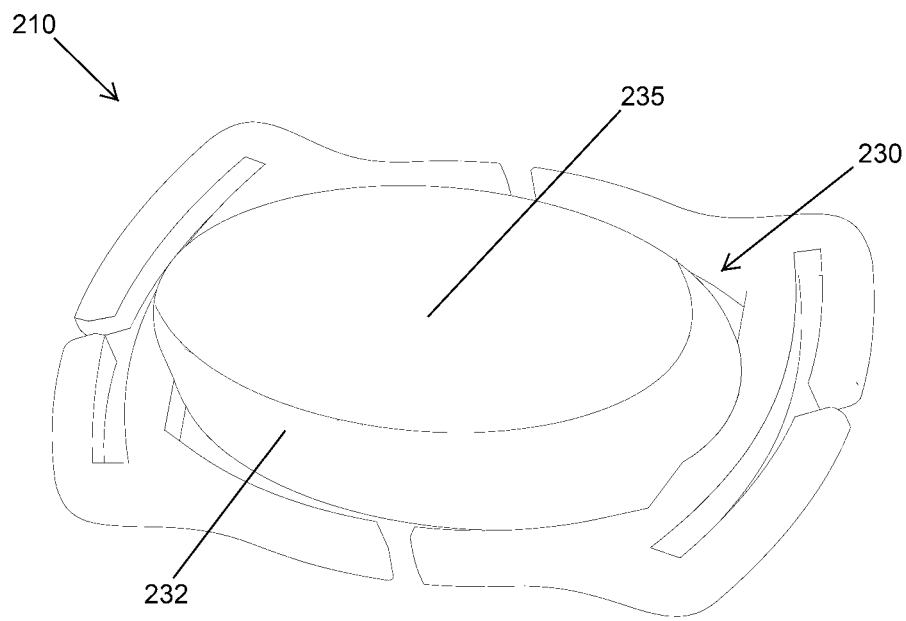
FIG. 6 is a perspective view diagram illustrating an exemplary apparatus for use with a diabetes management device, in accordance with some embodiments of the present invention.

Referring now to FIG. 5, according to some aspects of the present invention, a shell 130 of an apparatus 110 may include an enclosure wall 135 which may be adjacent to, or an extension of, a retention wall 132. In some embodiments, and as further illustrated, enclosure wall 135 may partially enclose one side of shell 130 (in this case, the top side), such that enclosure wall 135 may form an enclosure opening 136 which may, according to some aspects, be centrally aligned with a retention opening 131. According to other aspects, and with reference to FIG. 6, a shell 230 of an apparatus 210 may comprise an enclosure wall 235 which may fully enclose one side of shell 230 (in this case, the top side), such that no opening is formed in enclosure wall 235 and, thus, the retention opening (not illustrated) may only be visible on the bottom side of shell 230. As further illustrated in FIGS. 5 and 6, and in accordance with some embodiments, an enclosure wall (e.g., enclosure wall 135 or enclosure wall 235) of an apparatus may be shaped (e.g., rounded) so as to contour a diabetes management device when it is retained within the shell (e.g., shell 130 or shell 230) of the apparatus. In addition to limiting or preventing displacement of a diabetes management device retained in a shell, an enclosure wall may also be configured to at least partially protect (e.g., enclosure wall 135) or fully protect (e.g., enclosure wall 235) the diabetes management device.

Figure 7:
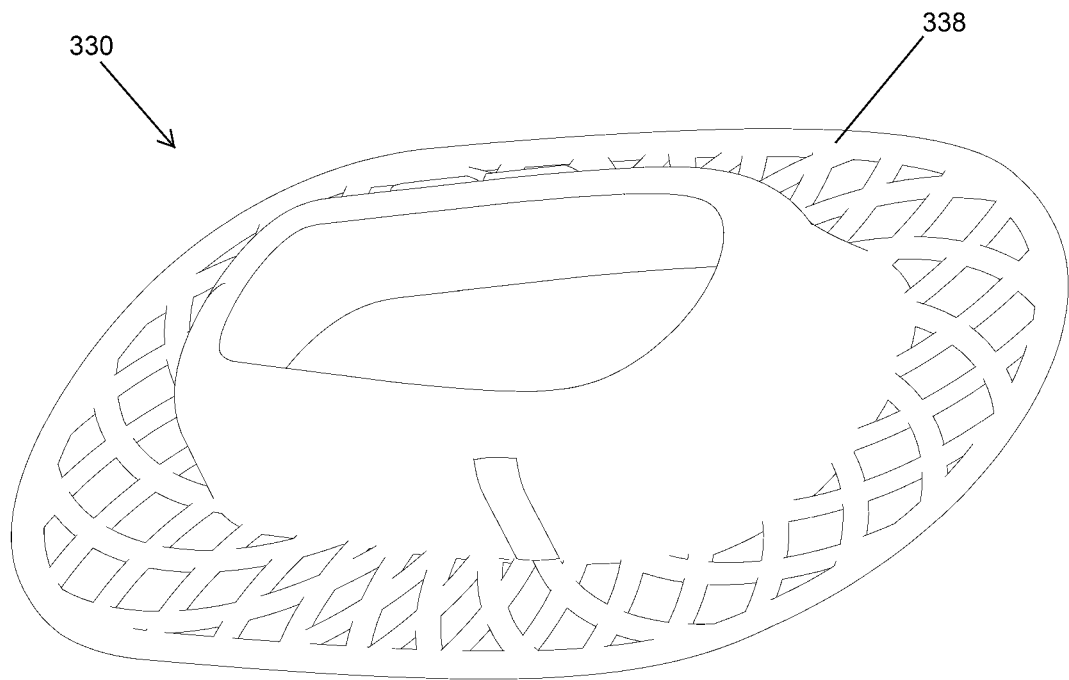
FIG. 7 is a perspective view diagram illustrating an exemplary shell of an apparatus for use with a diabetes management device, in accordance with some embodiments of the present invention.

Referring now to FIG. 7, and in accordance with some embodiments, a shell 330 may comprise an adhesion wall 338 which may be configured to be engaged with an adhesive patch. For example, in some embodiments, a top surface of adhesion wall 338 (i.e., the surface visible in FIG. 7) may be configured to adhere to an adhesive patch. As further illustrated in FIG. 7, adhesion wall 338 may comprise a plurality of holes formed, generally, into quadrilateral or triangular shapes. It is to be appreciated, however, that an adhesion wall may comprise a plurality of holes which may be formed into any shape to create various designs and patterns. For example, and without limitation, an adhesion wall of a shell may comprise a plurality holes formed into the shapes of stars and rectangles which may resemble that of a flag (see, e.g., FIG. 22).

Figure 11:
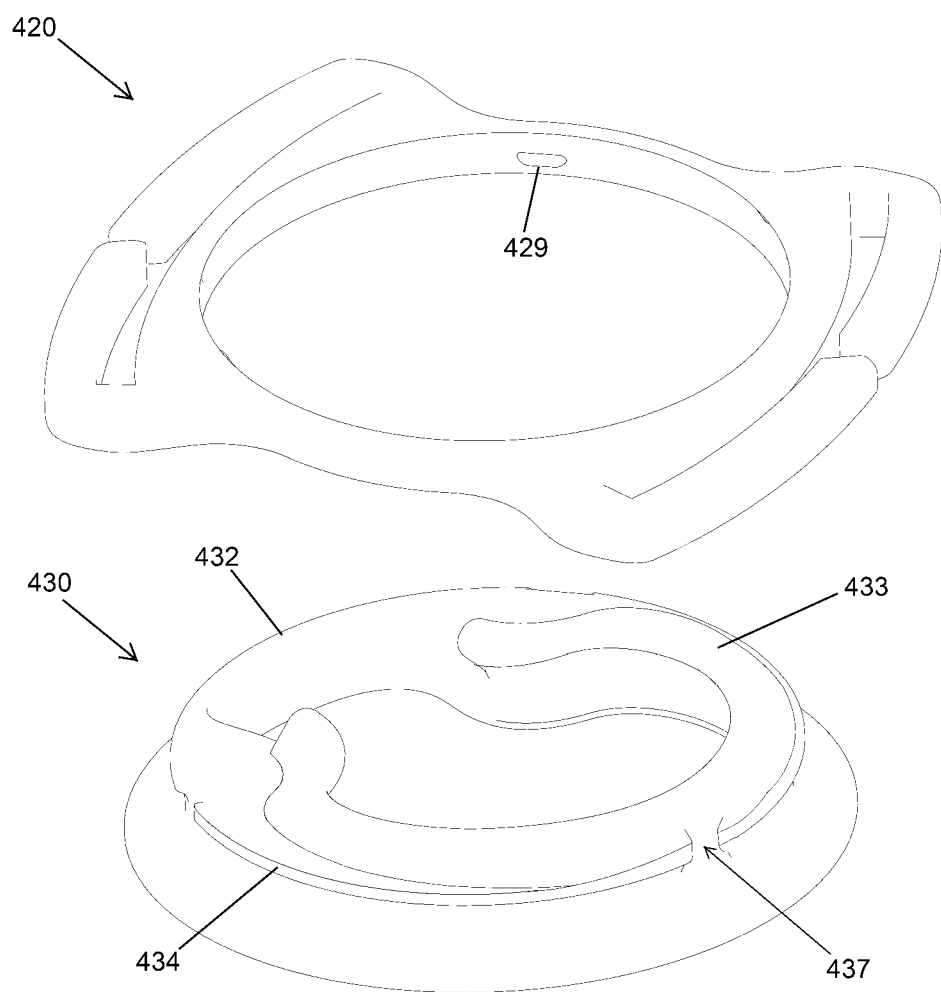
FIG. 11 is an exploded perspective view diagram illustrating an exemplary apparatus, comprising the shell of FIG. 9 and base of FIG. 10, for use with a diabetes management device, in accordance with some embodiments of the present invention.
Figure 12:
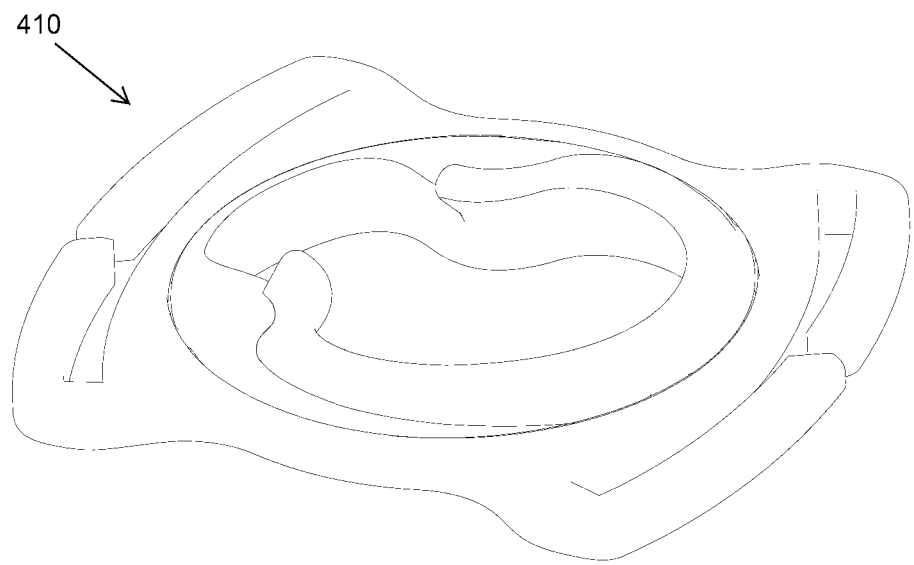
FIG. 12 is a perspective view diagram illustrating the apparatus of FIG. 11 with the shell of FIG. 9 and base of FIG. 10 connected together, in accordance with some embodiments of the present invention.

Referring now to FIGS. 9-12, and in accordance with some embodiments of the present invention, an apparatus 410 may comprise a base 420 having a base opening 427 which may be configured to receive shell 430 (or a portion thereof). Base 420 may comprise a base wall 428 having an inner surface which may define a perimeter of base opening 427. As more clearly illustrated in FIGS. 10 and 11, according to some aspects, a shape of base opening 427 may be generally the same as a shape of shell 430. For example, a shape formed by the perimeter of base opening 427 may be generally same as a shape formed by the perimeter of the lateral surface of retention wall 432. As further illustrated in FIGS. 10 and 11, and according to some embodiments, a plurality of tabs 429 may be formed on the inner surface of base wall 428 which may be configured to be received in corresponding grooves 437 of retention wall 432 of shell 430 such that shell 430 may be connected with base 420, as illustrated in FIG. 12. It is to be appreciated, however, that, according to other embodiments, a one or more grooves may be formed on an inner surface of a base wall which may be configured to be receive corresponding tabs on an outer surface of a retention wall of a shell. In some embodiments, a top or a bottom surface of a base may comprise one or more indicators corresponding to one or more tabs of the base. For example, a top surface of a base may comprise a plurality of arrows aligned with corresponding tabs on the inner surface of the base wall which may allow a user to locate the positions of the tabs when a shell is engaged with the base.

As more clearly illustrated in FIG. 11, shell 430 may also comprise a plurality of catch projections 434 extending along an outer surface of retention wall 432 and disposed between each of grooves 437. Catch projections 434 may protrude laterally from retention wall 432 by a distance that may about the same as a distance that tabs 429 protrude inwardly toward base opening 427 such that when shell 430 is engaged with base 420, shell 430 is flushly received therein (i.e., with a nominal amount of space between the inner surface of base opening 427 and the outer surface of retention wall 432). It is to be appreciated that when shell 430 is engaged with base 420, and base 420 (and/or shell 430) is rotated so that tabs 429 are not aligned with grooves 437, tabs 429 may be retained underneath catch projections 434 such that shell 430 may not be disengaged from base 420 (unless base 420 and/or shell 430 are rotated to realign tabs 429 with grooves 437). It is also to be appreciated that catch projections 434 may allow for free rotation of base 420 around shell 430 which, for example, may allow base 420 to rotate as needed when being worn by a user.

According to some embodiments of the present invention, one or more lateral sides of a base may have a pair of arms. In some aspects, a base may have two pairs of arms disposed on opposite sides of the base. For example, referring back now to FIG. 3, base 20 of apparatus 10 may comprise (i) a first arm pair having a first arm 21A and a second arm 22B, (ii) a second arm pair having a first arm 21B and a second arm 22B, (iii) a third arm pair having a first arm 21C and a second arm 22C, and (iv) a fourth arm pair having a first arm 21D and a second arm 22D, where the first arm pair is disposed at an opposite lateral side of base 20 to the second arm pair and where the third arm pair is disposed at an opposite lateral side of base 20 to the fourth arm pair. It is to be appreciated, however, that according to some embodiments, a base may have only one arm disposed at a lateral side.

As further illustrated in FIG. 3, a longitudinal axis of each arm may be generally parallel to a corresponding lateral side of base 20. Furthermore, and according to some embodiments, the first arm and the second arm in a pair of arms may be generally oriented such that the longitudinal axes of each are about coaxial. In accordance with other embodiments, and as further illustrated in FIG. 3, the first arm and the second arm in a pair of arms (e.g., first arm 21A and second arm 22A) may be curved such that the longitudinal axes of each are not coaxial. It is to be appreciated that, according to some embodiments, a pair of arms may be constructed from flexible material such that it may be configured to deform which may cause the relative positions of the arms in the pair of arms to change (thus also changing the relative positions of the longitudinal axes of each arm).

Figure 8:
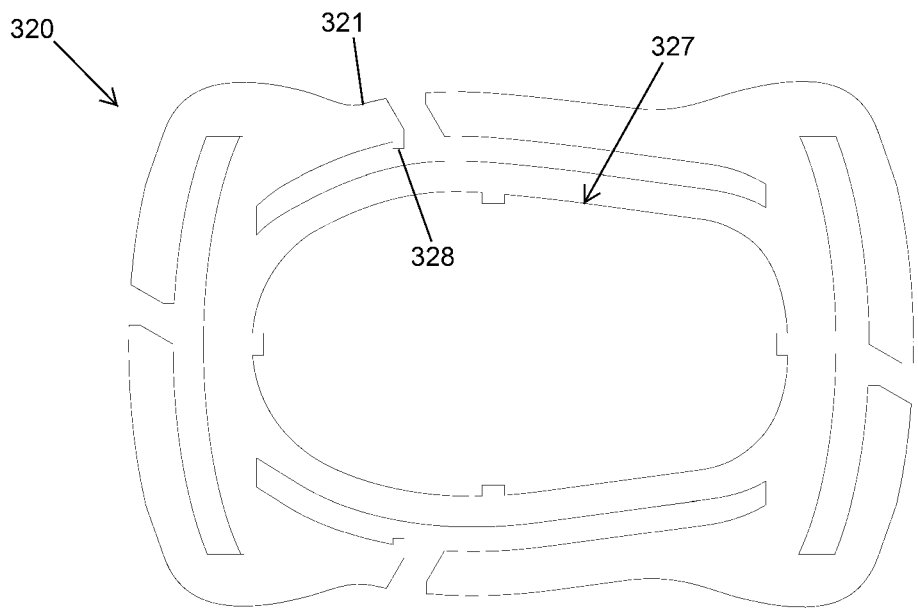
FIG. 8 is a perspective view diagram illustrating an exemplary base of an apparatus for use with a diabetes management device, in accordance with some embodiments of the present invention.

In some embodiments of the present invention, one or more arms of a base may have an exposed end. For example, as further illustrated in FIGS. 1 and 3, first arm 21A and second arm 22A may have an arm end 23A and 24A, respectively, which may be oriented such that each end may be adjacent to the other. According to some aspects, an end of an arm may be generally disposed near, or slightly offset from, a medial point of a lateral side of the base, as best illustrated, for example, in FIG. 3. According to other aspects, however, an end of an arm may be generally disposed near a distal end of a lateral side of the base. It is to be appreciated, however, that an end of an arm may be disposed anywhere along a lateral edge of a base. For example, as illustrated in FIG. 8, an end of an arm 321 of a base 320 may be disposed between a medial point and a distal point of a lateral side of base 320. In some embodiments, an arm may comprise one or more notches disposed at or near an end of the arm. For example, and as further illustrated in FIG. 8, a notch 328 may be disposed on an inner surface (i.e., the surface oriented toward a base opening 327) of arm 321.

According to some embodiments of the present invention, an end of an arm may comprise at least two noncoplanar surfaces. For example, as more clearly shown in FIG. 4, arm end 23A of first arm 21A may comprise a distal surface $D_1$ (i.e., the surface which is relatively further from retention opening 31) and a proximal surface $P_1$ (i.e., the surface which is relatively closer to retention opening 31). Likewise, arm end 24A of second arm 22A may comprise a distal surface $D_2$ and a proximal surface $P_2$. In some aspects, proximal surface $P_1$ of arm end 23A may be about parallel to distal surface $D_2$ of arm end 24A. Likewise, distal surface $D_1$ of arm end 23A may be about parallel to proximal surface $P_2$ of arm end 24A. It is to be appreciated, however, that a proximal surface of a first arm end in an arm pair may, in some embodiments, be about parallel to a proximal surface of a second arm end in the arm pair. Likewise, a distal surface of the first arm end in the arm pair may, in some embodiments, be about parallel to a distal surface of the second arm end in the arm pair.

Figure 4:
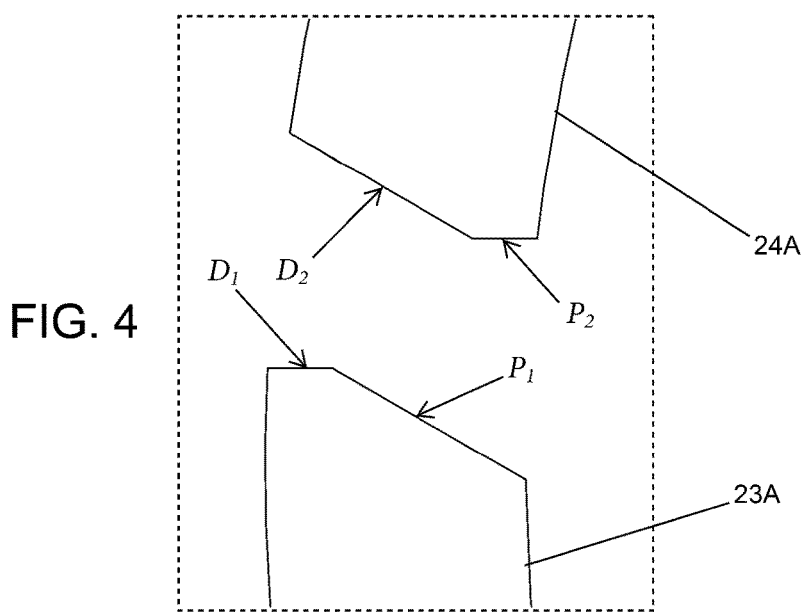
FIG. 4 is an enlarged view of detail S illustrated in FIG. 3, in accordance with some embodiments of the present invention.

Further to the above, and with reference to FIG. 4, it is also to be appreciated that distal surface $D_1$ and proximal surface $P_1$ of arm end 23A of first arm 21A may be about parallel to a proximal surface and a distal surface, respectively, of arm end 23B of first arm 21B. Likewise, distal surface $D_2$ and proximal surface $P_2$ of arm end 24A of second arm 22A may be about parallel to a proximal surface and a distal surface, respectively, corresponding to arm end 24B of second arm 22B. Furthermore, distal surface $D_1$ and proximal surface $P_1$ of arm end 23A of first arm 21A may be about parallel to the distal surface and the proximal surface, respectively, corresponding to arm end 24B of second arm 22B. Likewise, distal surface $D_2$ and proximal surface $P_2$ of arm end 24A of second arm 22A may be about parallel to the distal surface and the proximal surface, respectively, corresponding to arm end 23B of first arm 21B.

With further reference to FIG. 3, base 20 may comprise a plurality of band slots 25A, 25B, 25C, 25D which may be configured to receive and retain a band therein. Band slots 25A-D may be generally elongated openings disposed generally parallel to a lateral edge of base 20. As further illustrated, and according to some embodiments, band slots 25A-D may be generally defined by the openings formed by each arm pair. An end of a band (e.g., an end loop of an elastic band) may be received within any of band slots 25A-D, via an adjacent corresponding band aperture (described below), and may be retained therein unless removed by a user or by a sufficient external force (e.g., as a result of the band catching on an object). In some implementations, a first end of a band may be received in a first band slot at a first lateral side of a base (e.g., band slot 25A) and a second end of the band may be received in a second band slot on an opposing lateral side of the base (e.g., band slot 25B). It is to be appreciated, however, that an end of a band may be received in any or all band slots of a base in any configuration. An end of a band may be released from a band slot via a corresponding band aperture.

Referring further to FIG. 3, and in accordance with some embodiments of the present invention, base 20 may comprise a plurality of band apertures 26A, 26B, 26C, 26D which may be configured to receive and release a band. As illustrated, band apertures 26A-D may be generally defined by corresponding openings between the arm ends of an arm pair. For example, band aperture 26A may be defined by the opening between arm end 23A and arm end 24A of first arm 21A and second arm 22A, respectively. In some embodiments, one or more band apertures may be generally disposed near a medial point of each lateral side of a base. For example, as further illustrated in FIG. 3, band apertures 26A-D may be slightly offset from a medial point of each lateral side of base 20, with band apertures 26A and 26B being offset in relatively opposite directions and with band apertures 26C and 26D also being offset in relatively opposite directions. It is to be appreciated, however, that a band aperture may be disposed at any point along or near a lateral side of a base. For example, referring, briefly to FIG. 8, band apertures 326A and 326B of base 320 may be disposed further from a medial point of a lateral side, relative to the embodiment illustrated in FIG. 3. It is also to be appreciated that two band apertures disposed at opposing lateral sides of a base may be relatively offset from a line which may be aligned with a common point on each lateral side (e.g., centerline CL illustrated in FIG. 3, explained in more detail below). However, according to some embodiments, two band apertures disposed at opposing lateral sides of a base may be aligned along a line through a common point on each lateral side, as also illustrated in FIG. 8.

It is to be appreciated that, while a band aperture may generally allow a user to guide a portion of a band therethrough, the band aperture may also be configured to allow a portion of a band to pass through the aperture if, for example, the band is being pulled by an external force directed generally toward the band aperture. It is also to be appreciated that the positioning of the band apertures along the lateral sides of the base may also serve to prevent deformation and breakage of the arms, or other portions of the base (if, for example, the base is constructed from a rigid material). For example, referring again to FIG. 3, by aperture 26A being slightly offset toward an upper end (i.e., toward the top of FIG. 3) from a lengthwise centerline C and by aperture 26B being slightly offset toward an lower end (i.e., toward the bottom of FIG. 3) from centerline C, movement of a band (not illustrated) retained in band slots 25A and 25B in a direction toward band apertures 26A and/or 26B may be influenced by the positions of band apertures 26A and 26B such that a force on first arm 21A and second arm 22A may not be directly opposed by the force on first arm 21B and second arm 22B (thus avoiding compounding forces exerted on either side of base 20).

Further to the above, it is also to be appreciated that the dual, noncoplanar surfaces of the arm ends may also serve a purpose in directing the movement of a band through an aperture. For example, with further reference to FIGS. 3 and 4, distal surface $D_2$ and proximal surface $P_1$ each have an angle which may configured to cause a band moving into or out of band slot 25A to be forced downward (i.e., toward the bottom of FIG. 3) or upward (i.e., toward the top of FIG. 3), respectively. Additionally, and as can be further appreciated by the illustration of FIG. 4, the positioning and angles of distal surface $D_1$ and proximal surface $P_2$ may also influence the direction of a band moving through band aperture 26A. For instance, a band moving into band aperture 26A may partially contact distal surface $D_1$, which may apply a force generally in the direction of distal surface $D_2$, thus increasing the influence of distal surface $D_2$ in forcing the band in a downward direction. Similar mechanisms can be visualized in band apertures 26B-D (also illustrated in FIG. 3). As can be further visualized in FIG. 3, the configuration of band apertures 26A and 26B may allow a band to be released at slightly different angles. For example, a band being forced out of band slots 25A and 25B (i.e., toward the left and right, respectively, relative to FIG. 3) may be guided slightly upward and downward, respectively, as it passes through band apertures 26A and 26B, respectively.

It is to be appreciated that the arms and the corresponding band slot of an apparatus may also play a role in directing the movement of a band from the band slot through a corresponding band aperture. As further illustrated in FIG. 3, for example, the curvature of a pair of arms (e.g., first arm 21A and second arm 22A) and a corresponding band slot (e.g., band slot 25A) may cause a band received within the band slot to be directed toward a corresponding band aperture when the band is forced, generally, toward the band aperture and away from the apparatus (e.g., toward the left of FIG. 3). Furthermore, if a pair of arms is constructed from flexible material, a band (which may be initially received within a corresponding band slot) being forced toward a corresponding band aperture may cause deformation of the arms which may widen the band aperture and further aid in the forcing of the band toward the band aperture to be released therethrough.

Figure 13:
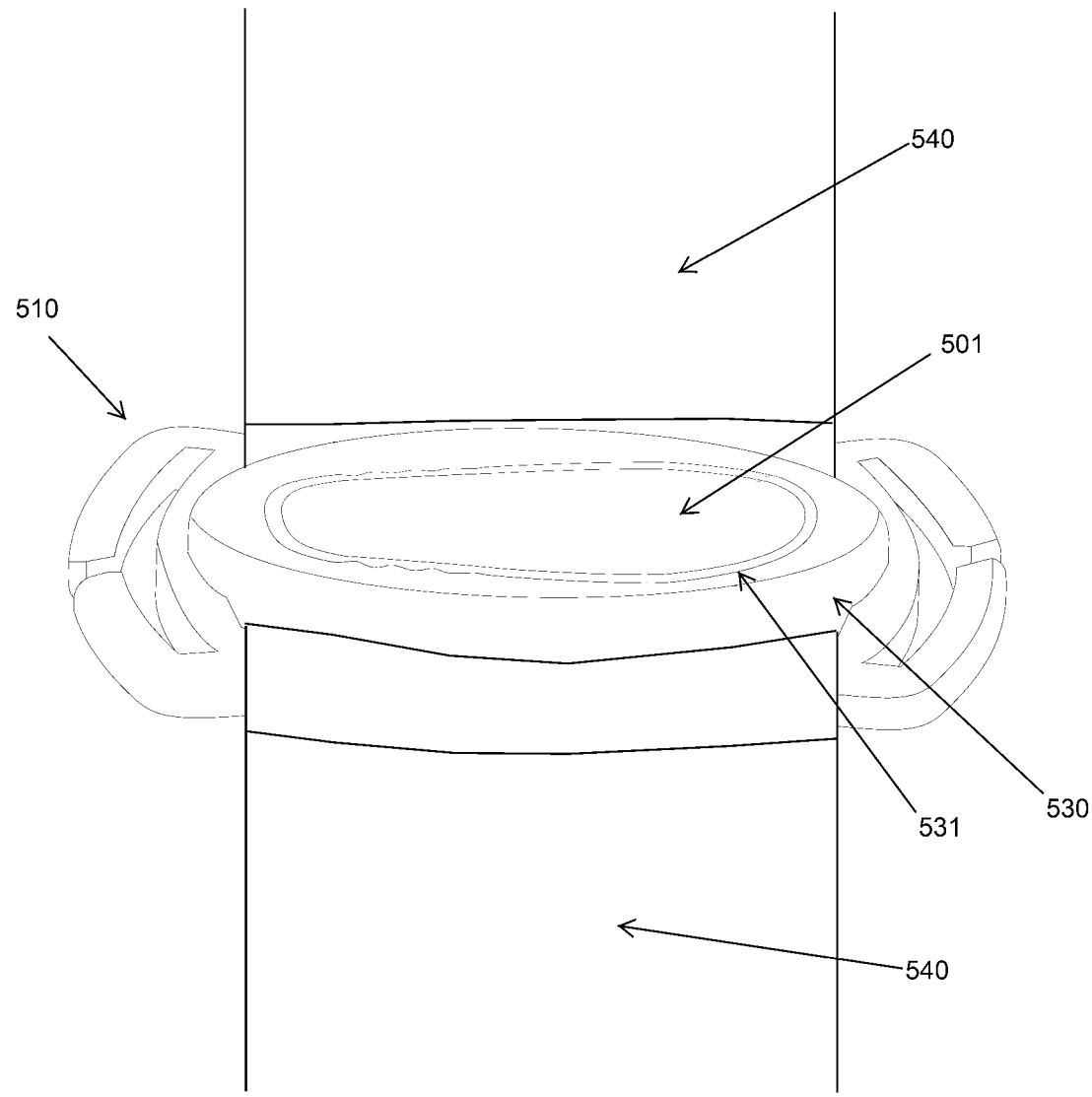
FIG. 13 is a perspective view diagram illustrating the apparatus of FIG. 1, an exemplary diabetes management device retained in the shell of the apparatus, and an exemplary band attached to the apparatus, in accordance with some embodiments of the present invention.

According to some implementations of the present invention, an apparatus, or components thereof, may be used as part of a system for protecting and securing a diabetes management device. In some embodiments, a system may include a base, a shell, a diabetes management device, and a band, or combinations thereof. For example, referring to FIG. 13, according to one implementation, a system may comprise an apparatus 510, a diabetes management device 501, and a band 540 (partially illustrated) which may secured to a portion of a user's body. As illustrated, diabetes management device 501 may be retained within a retention opening 531 of shell 530 of apparatus 510, with a first end of band 540 attached to a first pair of arms (not illustrated) of apparatus 510 and a second end of band 540 attached to a second pair of arms (not illustrated) of apparatus 510, and with a portion of each end of band 540 being retained within corresponding band slots (not illustrated).

Figure 14:
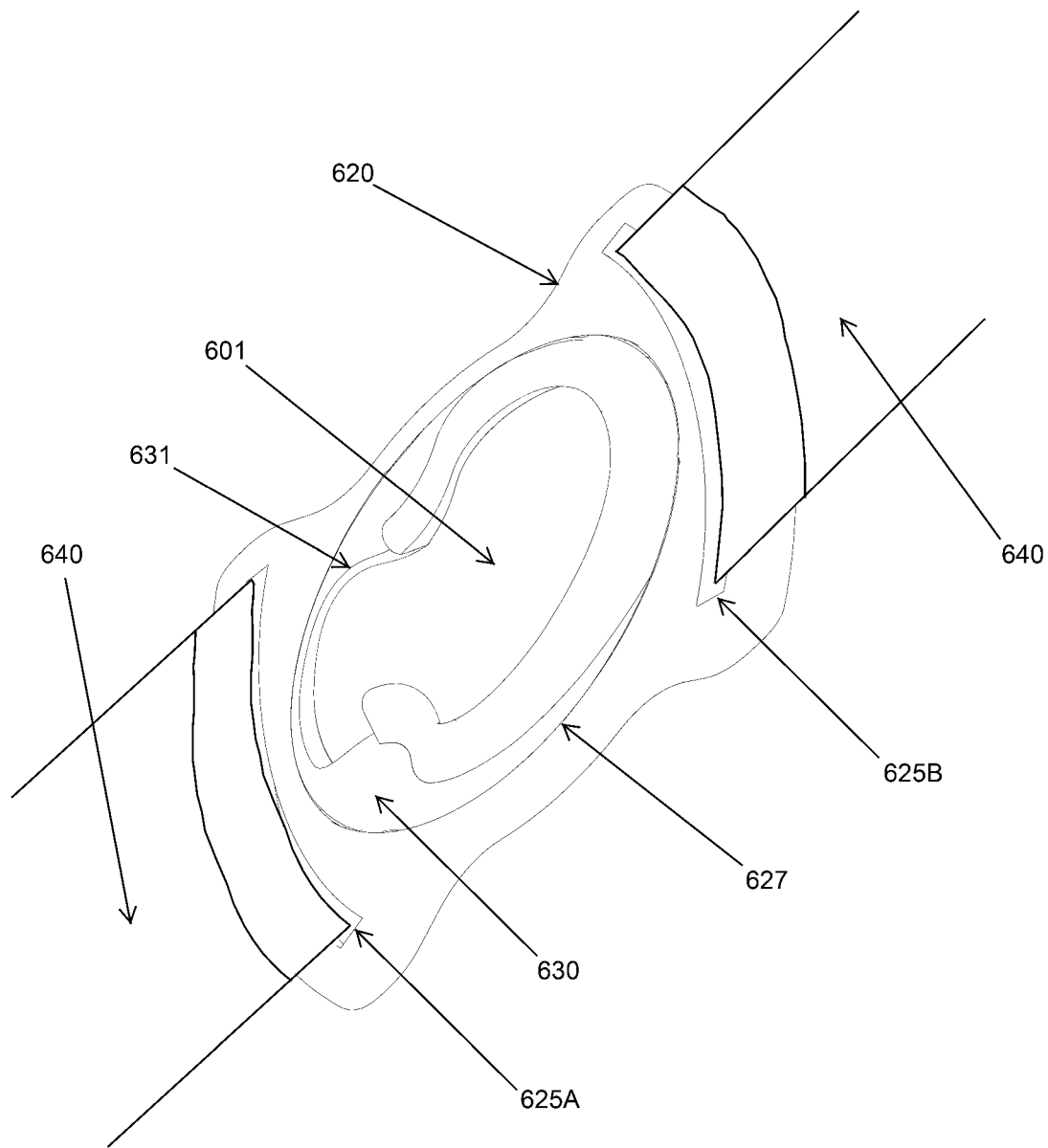
FIG. 14 is a perspective view diagram illustrating the apparatus of FIG. 12, an exemplary diabetes management device retained in the shell of the apparatus, and an exemplary band attached to the apparatus, in accordance with some embodiments of the present invention.

According to another implementation of the present invention, and referring now to FIG. 14, a system may comprise an apparatus 610, a diabetes management device 601, and a band 640, wherein a base 620 and a shell 630 are removable connected. As illustrated, diabetes management device 601 may be retained within a retention opening 631 of shell 630 of apparatus 610 and shell 630 may be retained within a base opening 627 of base 620. A first end of band 640 may be attached to a first pair of arms (not illustrated) of base 620 and a second end of band 640 may be attached to a second pair of arms (not illustrated) of base 620, with a portion of each end of band 640 being retained within band corresponding band slots 625A and 625B.

According to some implementations of the present invention, system for securing and protecting a diabetes management device may further include an adhesive patch. An adhesive patch may be generally circular or oval shaped, or any other shape, and may be constructed from a flexible material. In some embodiments, an adhesive patch may comprise an adhesive layer configured to adhere to a user's skin or diabetes management device. According to some aspects, an adhesive layer may contain a hypoallergenic adhesive. An adhesive patch may also comprise one or more liners and/or covers which, according to some embodiments, may be overlaid on an adhesive layer.

In some embodiments, an adhesive patch may be water-resistant or waterproof such that it may be configured to protect a diabetes management device from water, or to prevent the intrusion thereof. For example, a waterproof adhesive patch may be applied over a diabetes management device being worn on a user's skin such that the adhesive patch adheres to, and completely covers, the diabetes management device and a portion of the user's skin adjacent to the diabetes management device. It is to be appreciated that an adhesive patch may be adapted to allow a user to apply the patch easily and without making contact with an adhesive layer. Furthermore, an adhesive patch may be adapted such that a user may apply the patch using one hand.

According to some embodiments, an adhesive patch may comprise one or more liners on a bottom side of the patch, overlaid on an adhesive layer. In some aspects, an adhesive layer may be completely overlaid by one or more liners whereas, and according to other aspects, an adhesive layer may be partially overlaid by one or more liners. For example, a bottom side of a patch may comprise a plurality of liners arranged around a center of the patch which may comprise an exposed area of an adhesive layer for adhering to a diabetes management device. To apply the patch, it may be placed over a diabetes management device being worn on a user's skin, with the bottom side of the patch towards the user's skin and with the center of the patch over the top of the diabetes management device. Then, the user may remove the liners to expose the remaining portions of the adhesive layer and apply the remaining adhesive layer to the user's skin immediately adjacent to the diabetes management device. In some embodiments, an adhesive patch may also comprise one or more removable covers on a top side of the patch which may protect a top layer of the patch until the patch is applied to a user's skin and/or diabetes management device. In some implementations, a patch may be applied to a user's skin for about four to about six hours before exposing the patch to moisture.

Figure 15:
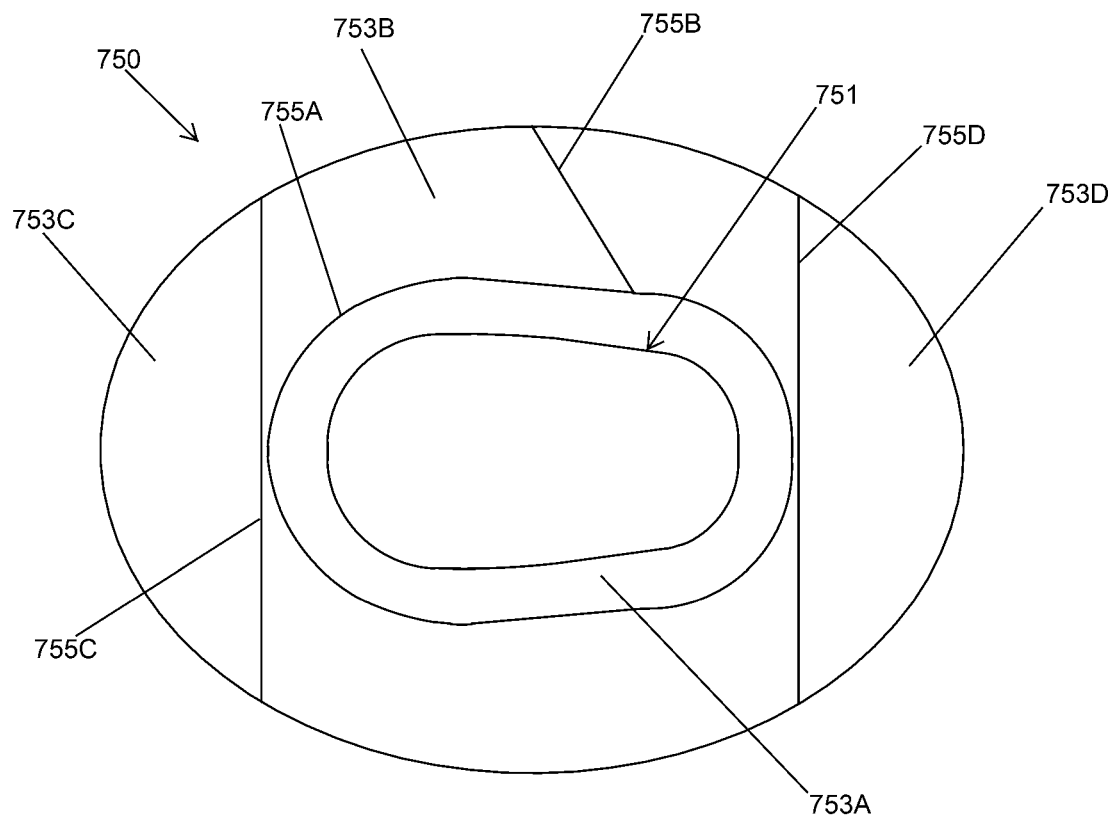
FIG. 15 is a bottom view diagram illustrating an exemplary adhesive patch, in accordance with some embodiments of the present invention.
Figure 16:
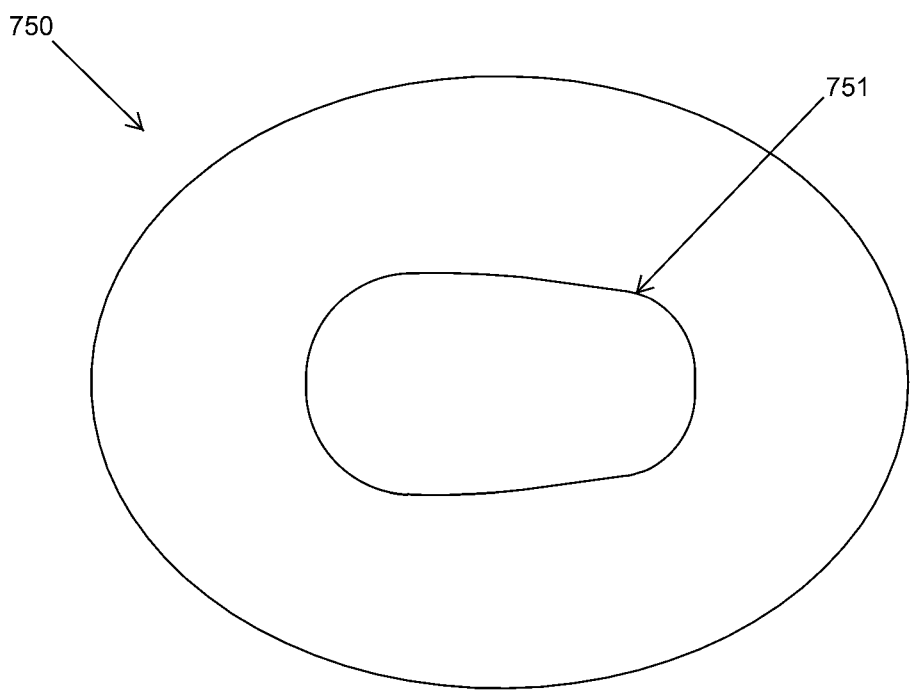
FIG. 16 is a top view diagram illustrating the patch of FIG. 15, in accordance with some embodiments of the present invention.
Figure 17:
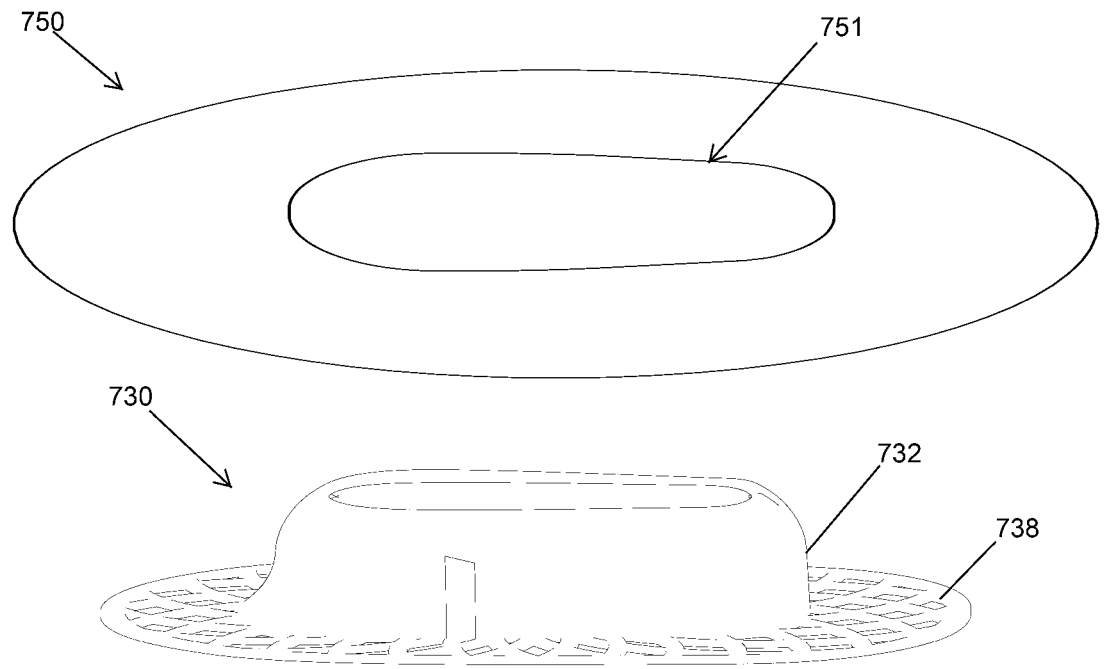
FIG. 17 is an exploded perspective view diagram illustrating an exemplary system comprising the patch of FIG. 15 and the shell of FIG. 7, in accordance with some embodiments of the present invention.

In some embodiments, an adhesive patch may have an opening formed therein through which a shell (or portion thereof) of an apparatus may be disposed. For example, referring to FIGS. 15 and 16, a patch 750, which may be configured for use with a shell of an apparatus, may be shaped, generally, as an oval having a patch opening 751 which, according to some embodiments, may be shaped according to a shape formed by a retention wall of a shell. Patch 750 may comprise a bottom side (illustrated in FIG. 15) and a top side (illustrated in FIG. 16), with the bottom side having an adhesive layer overlaid with a plurality of liners 753A, 753B, 753C, and 753D separated by a plurality of cutlines 755A, 755B, 755C, and 755D. As illustrated in FIG. 15, liner 753A may circumscribe patch opening 751 and liner 753B may circumscribe liner 753A. In addition, liners 753C and 753D may each be disposed at or near lateral ends of patch 750 and adjacent to liner 753B. To remove a liner, a user may peel back a portion of a liner along an edge of patch 750 and/or along a cutline to expose the adhesive layer. The adhesive layer of patch 750 may be adapted to adhere a user's skin, a shell, and/or a base.

Figure 18:
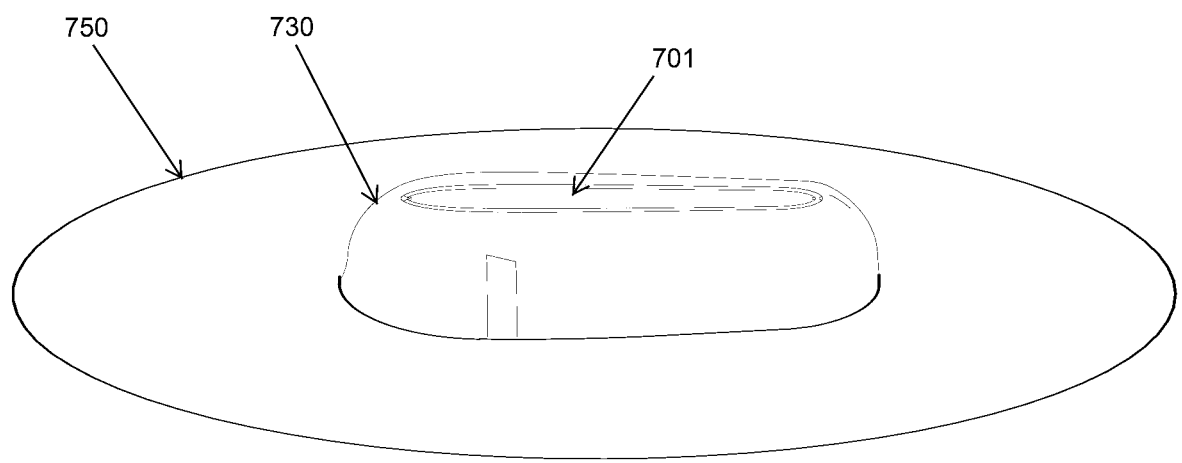
FIG. 18 is a perspective view diagram illustrating the system of FIG. 17, with the patch of FIG. 15 adhered to the shell of FIG. 7, in accordance with some embodiments of the present invention.

According to some implementations, a patch may be applied by removing liners in a particular order and adhering the patch to a shell and a user's skin in a particular order. For example, in one implementation, and with reference to FIGS. 15-18, to apply patch 750, a user may first remove liner 753A to expose a first area of the adhesion layer adjacent to patch opening 751. The user may then place patch 750 around a shell 730, with the bottom side of patch 750 (i.e., the side having the adhesion layer) toward an adhesion wall 738 of shell 730, such that a retention wall 732 thereof is received through patch opening 751 (as illustrated in FIG. 18). Next, the user may then press patch 750 down on adhesion wall 738 to cause the first area of the adhesion layer to adhere to adhesion wall 738. Then, the user may remove liner 753B to expose a second area of the adhesion layer (e.g., by turning patch 750 and shell 730 over, beforehand, to access the patch liners). Following, the user may place shell 730 and patch 750 over an application area of the user's skin (not illustrated), where a diabetes management device 701 is being worn. The user may then secure shell 730 around diabetes management device 701, such that it is retained within retention opening 731, and press down on patch 750 such that the second area of the adhesion layer adheres to the application area. Lastly, the user may remove liners 753C and 753D from each end of patch 750 to expose a third and a fourth area of the adhesion layer and then press down on patch 750 to cause the third and fourth area of the adhesion layer to adhere to the application area.

Figure 19:
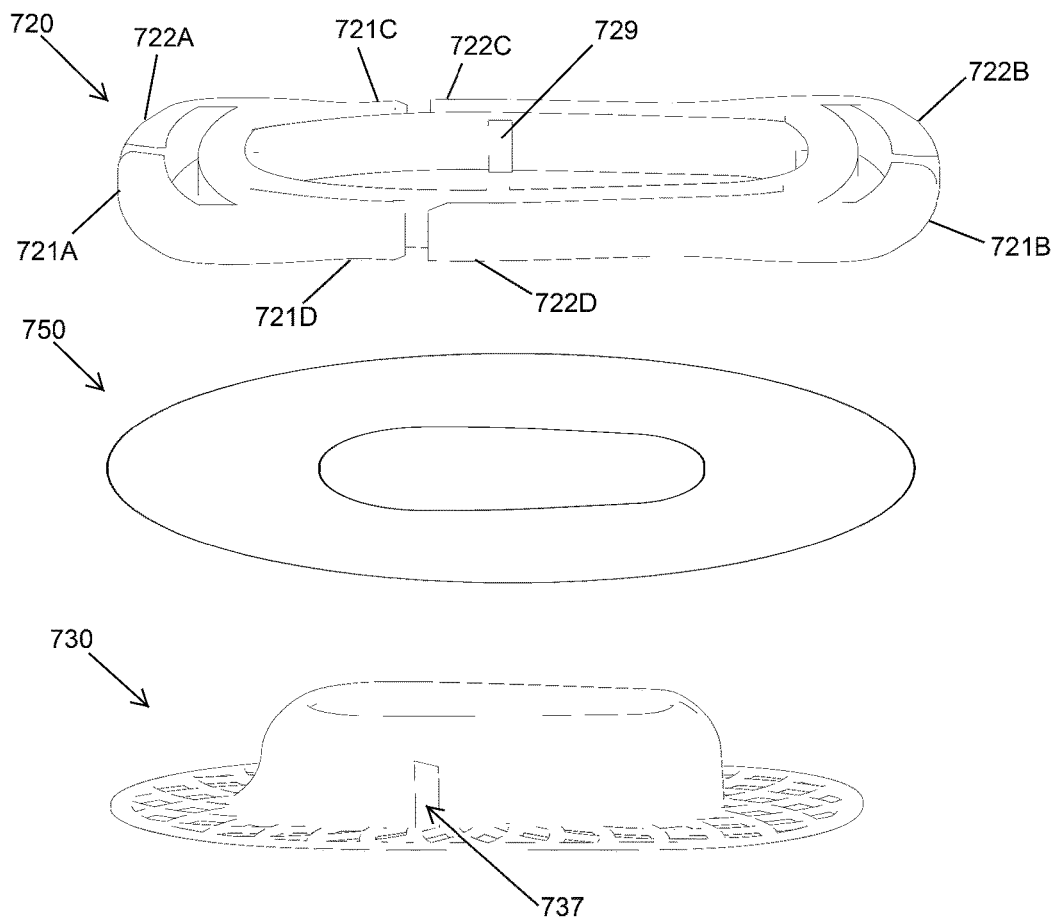
FIG. 19 is an exploded perspective view diagram illustrating an exemplary system comprising the base of FIG. 8, the patch of FIG. 15, and the shell of FIG. 7, in accordance with some embodiments of the present invention.
Figure 20:
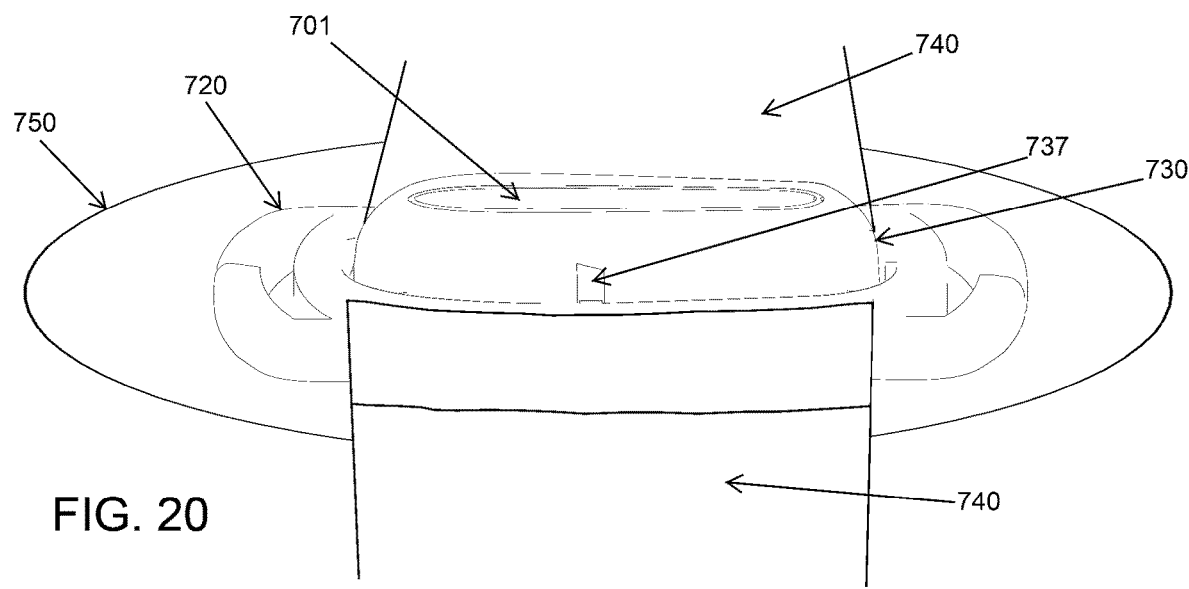
FIG. 20 is a perspective view diagram illustrating the exemplary system of FIG. 19 with an exemplary band attached to the base, in accordance with some embodiments of the present invention.
Figure 21:
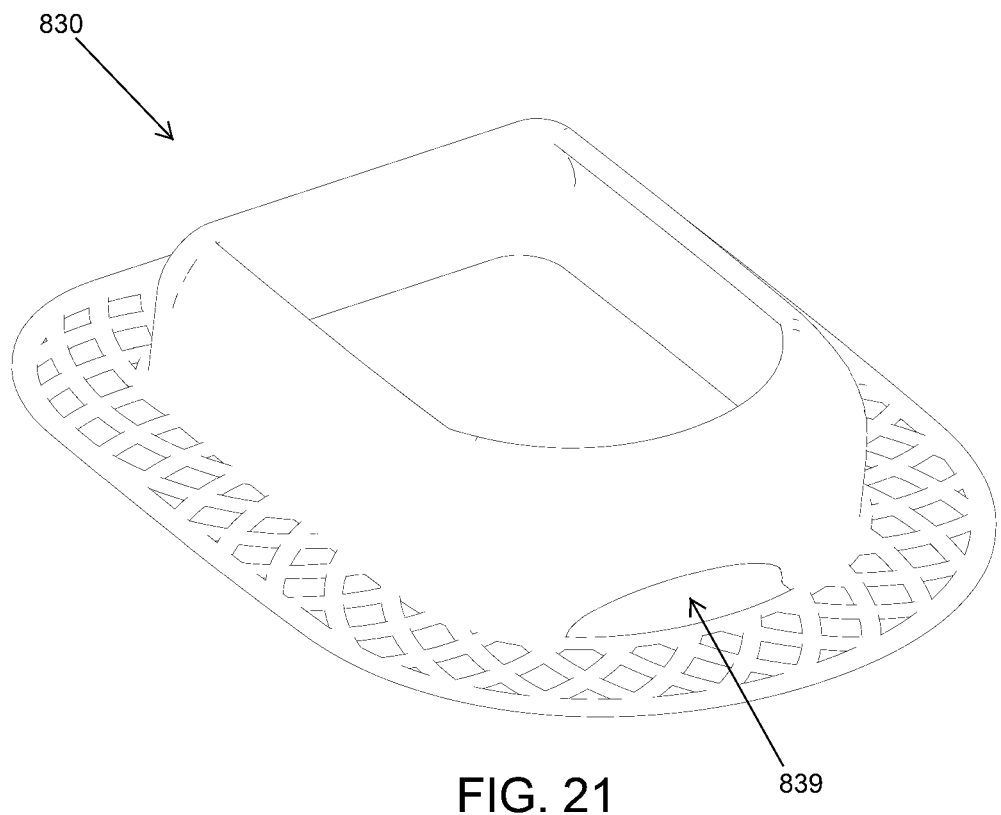
FIG. 21 is a perspective view diagram illustrating an exemplary apparatus for use with a diabetes management device, in accordance with some embodiments of the present invention.
Figure 22:
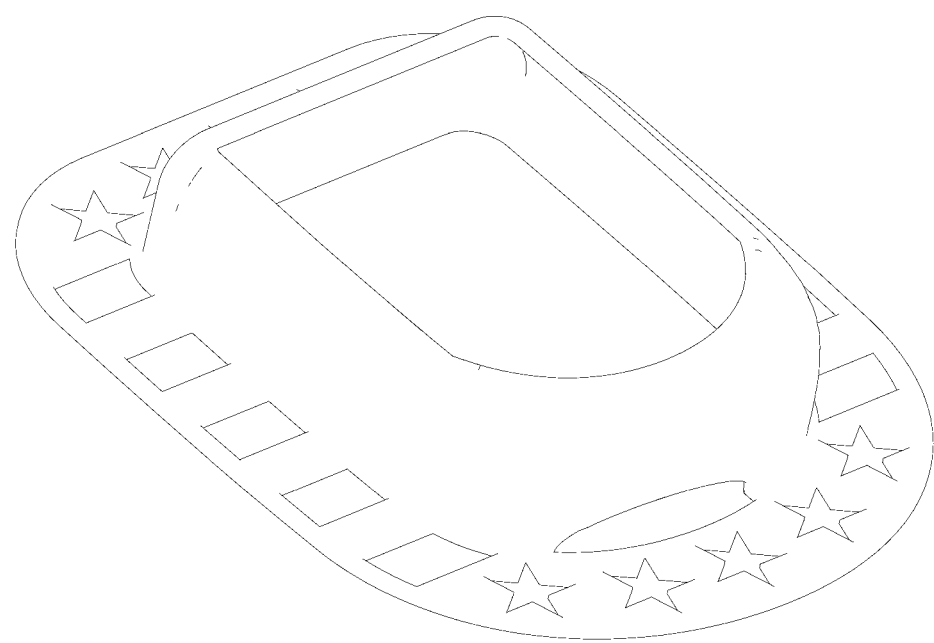
FIG. 22 is a perspective view diagram illustrating an exemplary apparatus for use with a diabetes management device, in accordance with some embodiments of the present invention.
Figure 23:
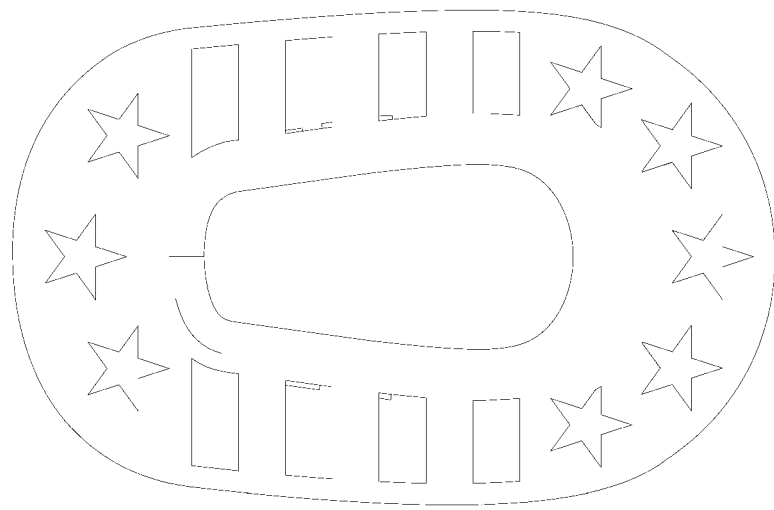
FIG. 23 is a bottom view diagram illustrating an exemplary apparatus for use with a diabetes management device, in accordance with some embodiments of the present invention.
Figure 24:
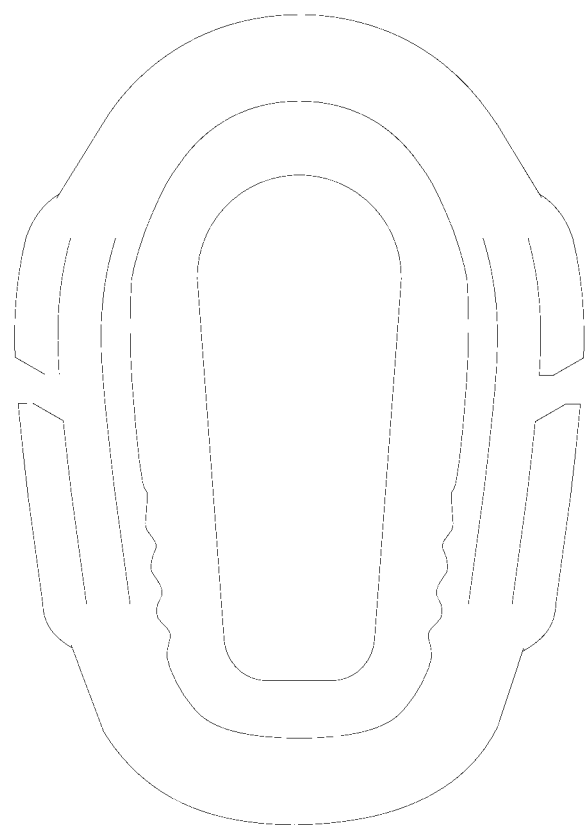
FIG. 24 is a bottom view diagram illustrating an exemplary apparatus for use with a diabetes management device, in accordance with some embodiments of the present invention.
Figure 25A:
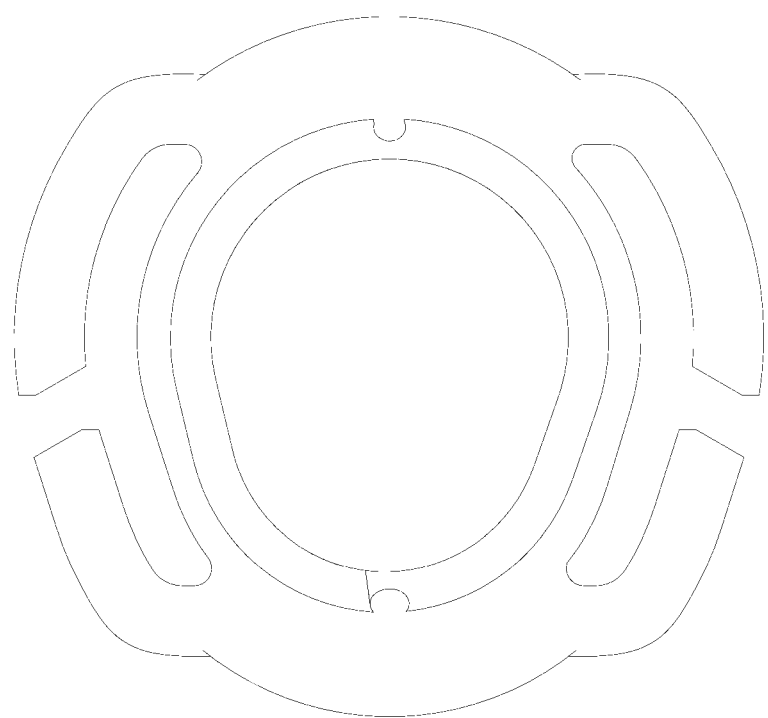
FIGS. 25A and 25B are bottom and top perspective view diagrams, respectively, illustrating an exemplary apparatus for use with a diabetes management device, in accordance with some embodiments of the present invention.
Figure 25B:
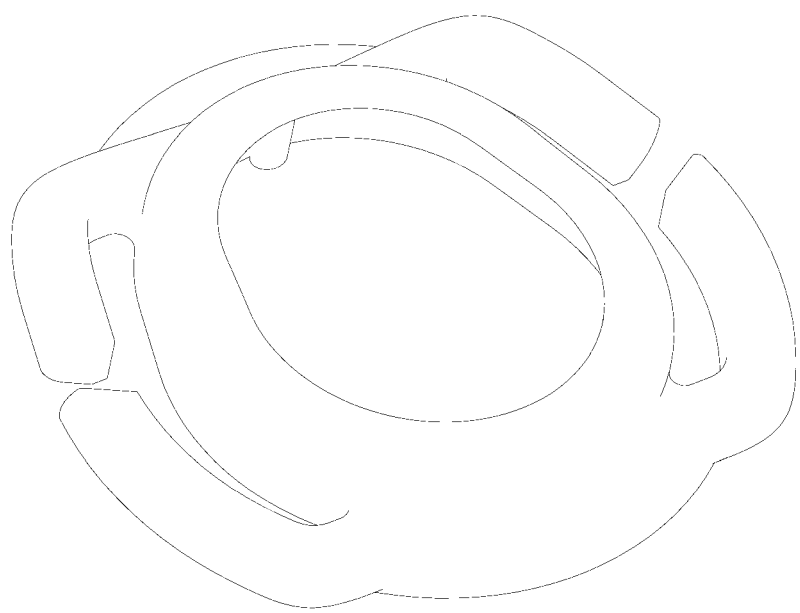
Figure 26:
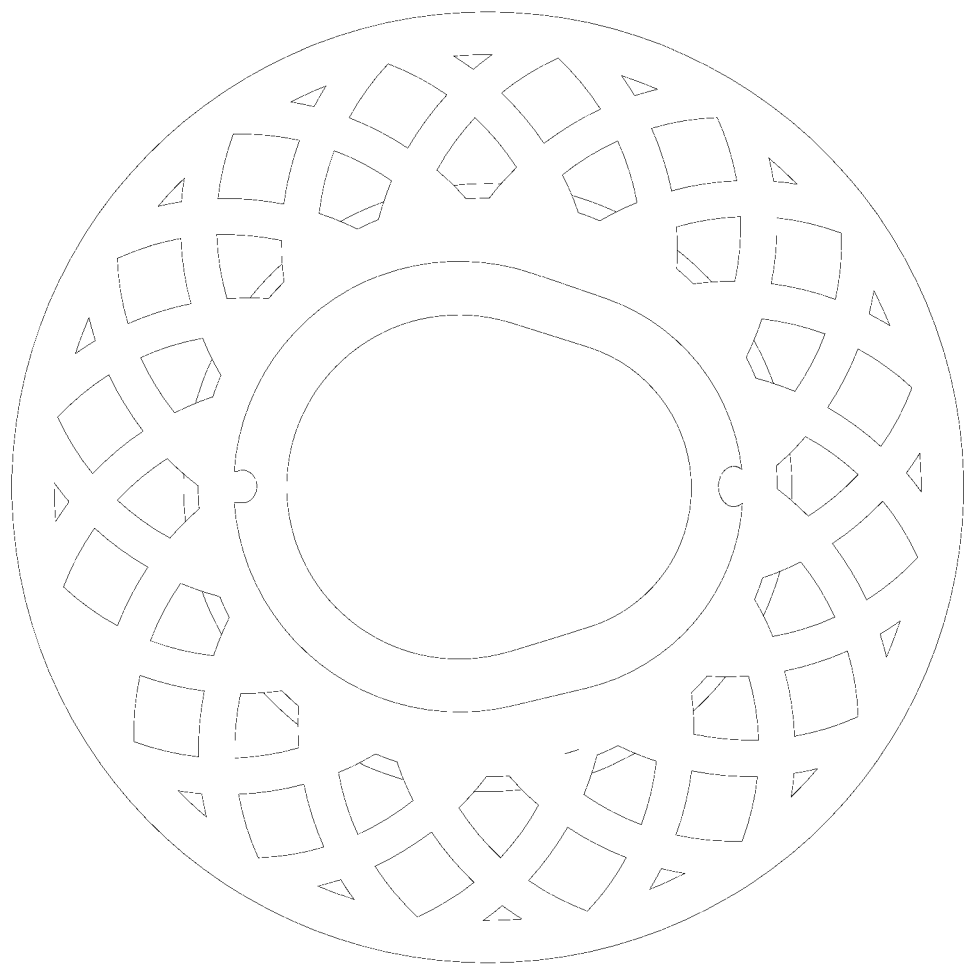
FIG. 26 is a bottom view diagram illustrating an exemplary apparatus for use with a diabetes management device, in accordance with some embodiments of the present invention.
Figure 27:
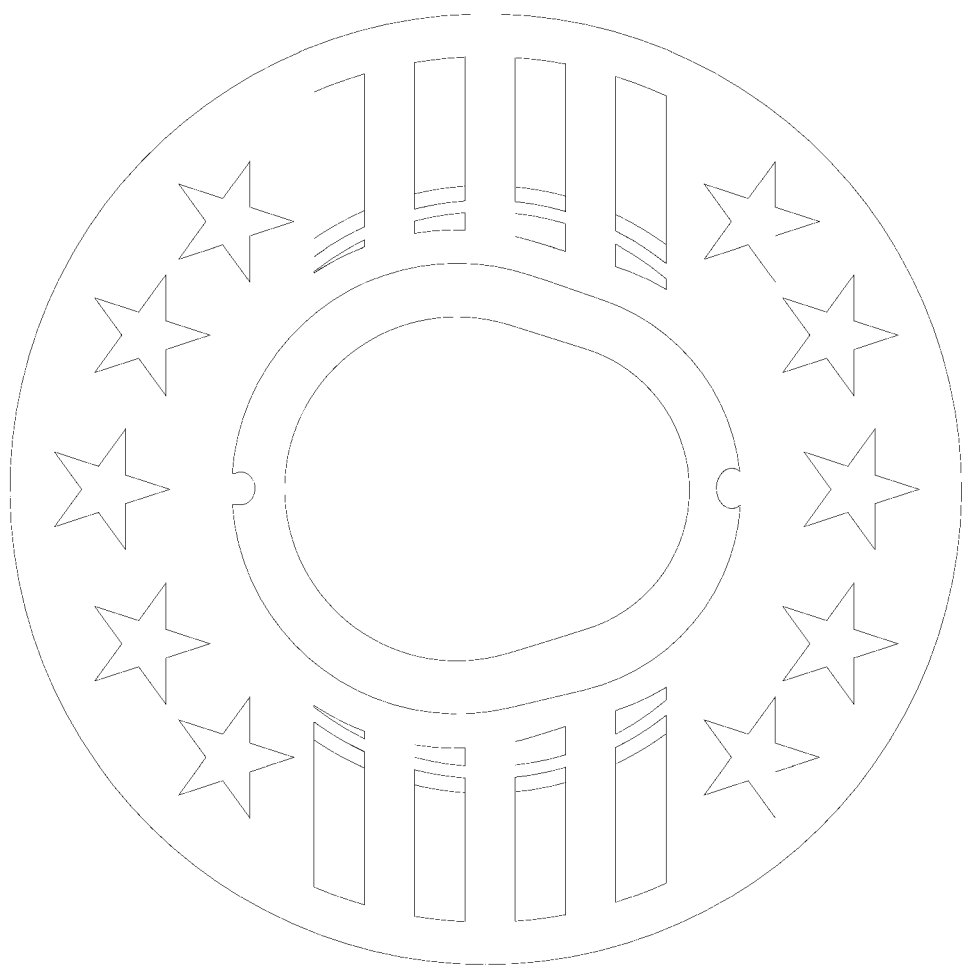
FIG. 27 is a bottom view diagram illustrating an exemplary apparatus for use with a diabetes management device, in accordance with some embodiments of the present invention.
Figure 28A:
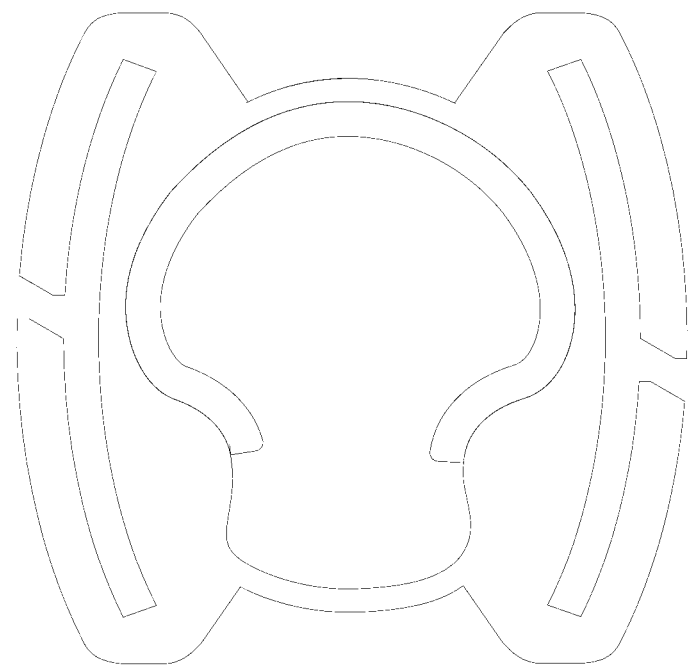
FIGS. 28A and 28B are bottom and top perspective view diagrams, respectively, illustrating an exemplary apparatus for use with a diabetes management device, in accordance with some embodiments of the present invention.
Figure 28B:
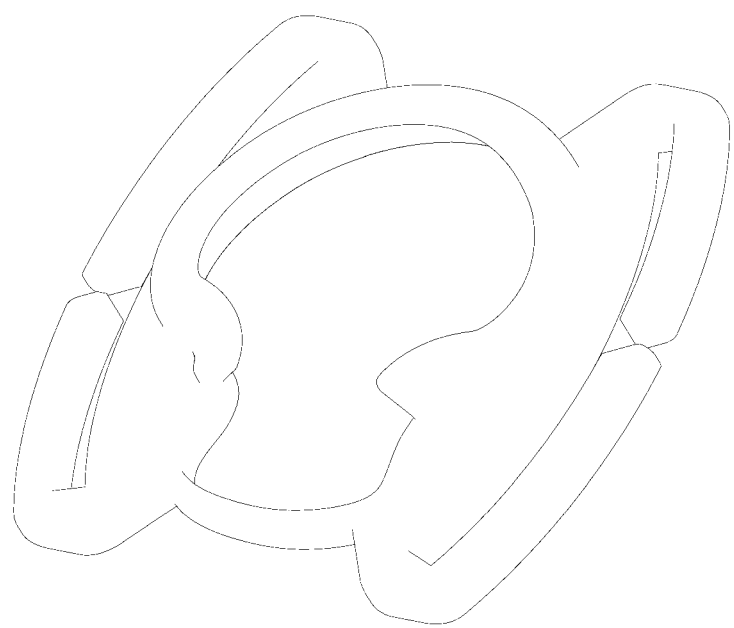
Figure 29:
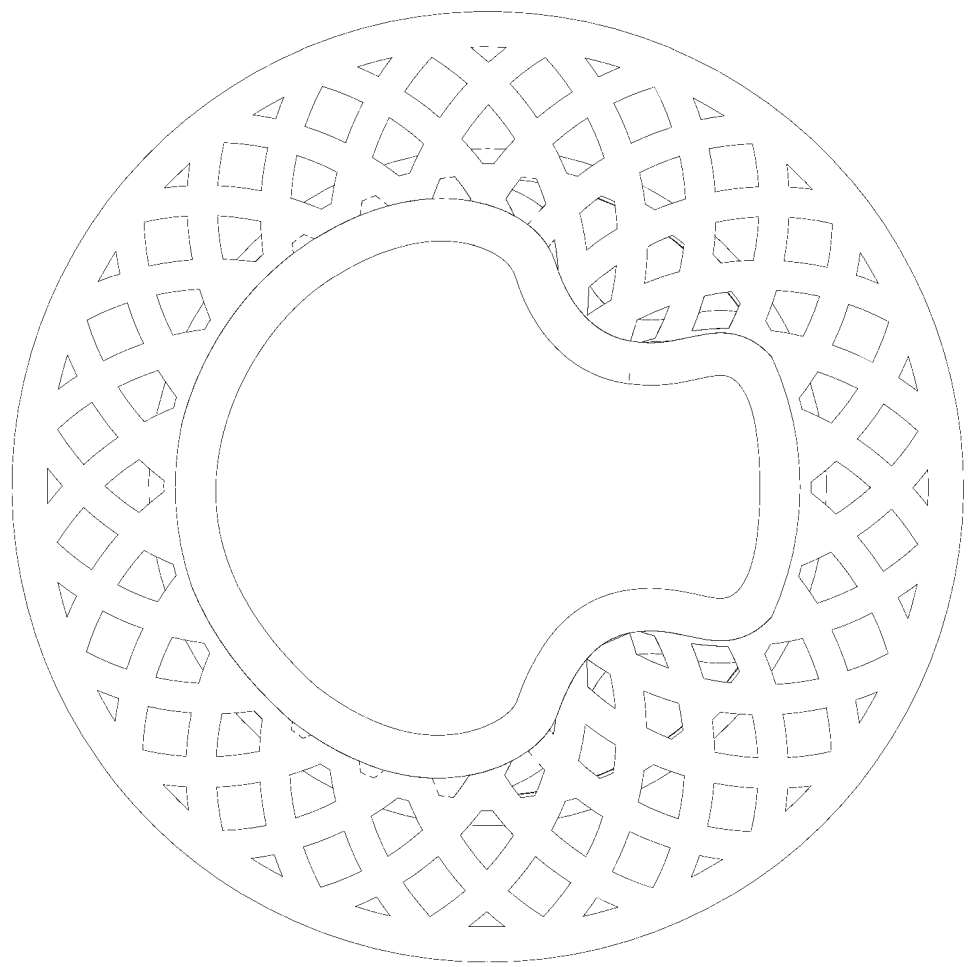
FIG. 29 is a bottom view diagram illustrating an exemplary apparatus for use with a diabetes management device, in accordance with some embodiments of the present invention.
Figure 30:
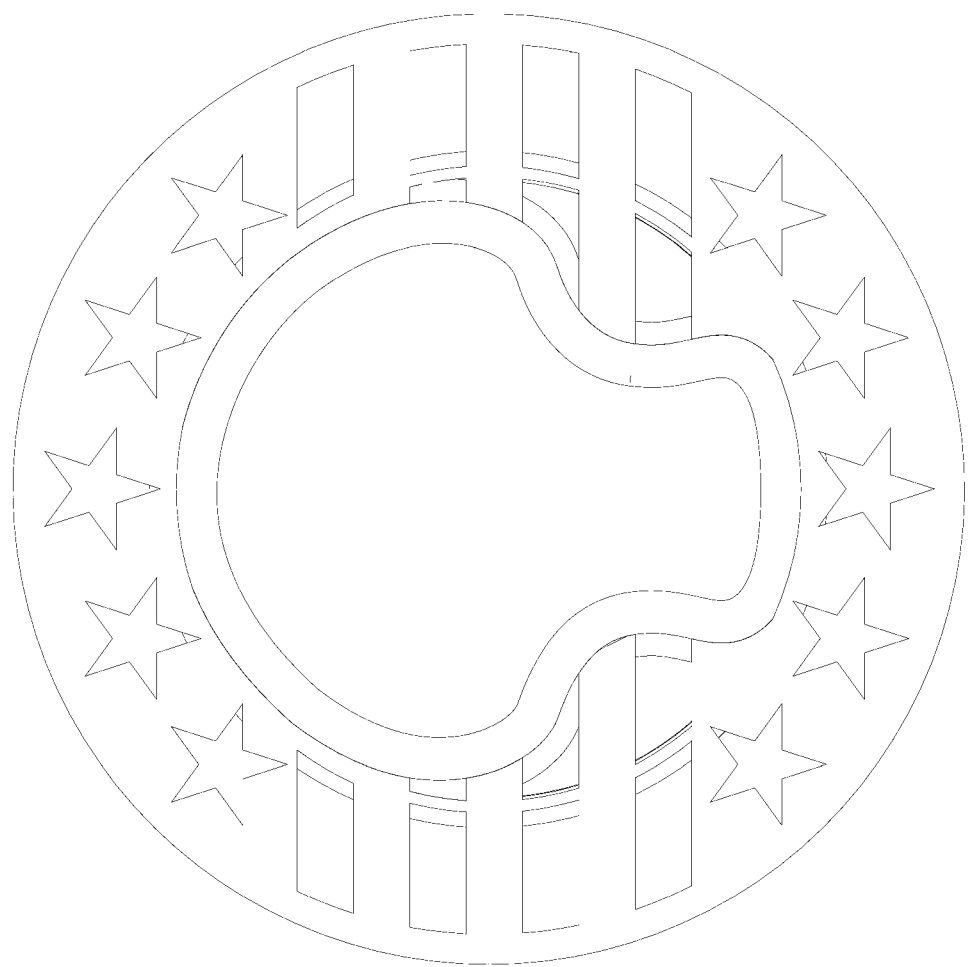
FIG. 30 is a bottom view diagram illustrating an exemplary apparatus for use with a diabetes management device, in accordance with some embodiments of the present invention.
Figure 31A:
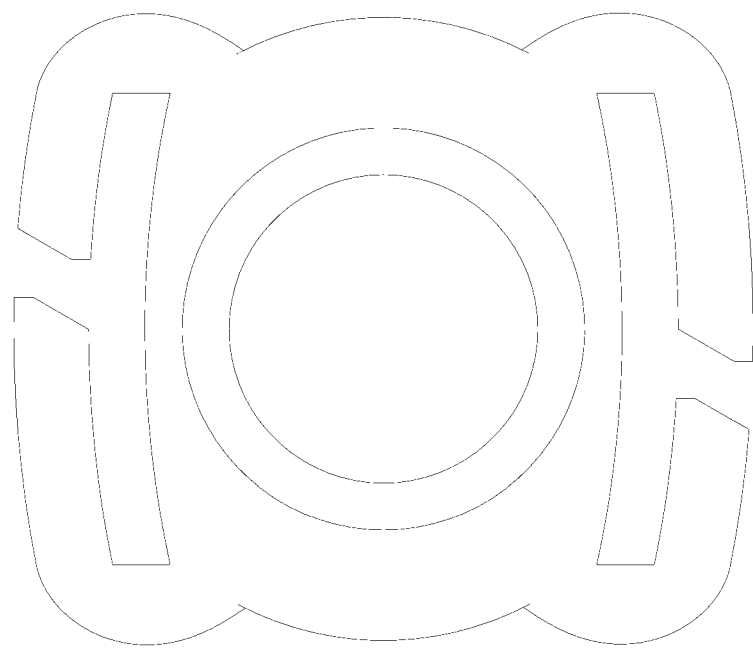
FIGS. 31A and 31B are bottom and top perspective view diagrams, respectively, illustrating an exemplary apparatus for use with a diabetes management device, in accordance with some embodiments of the present invention.
Figure 31B:
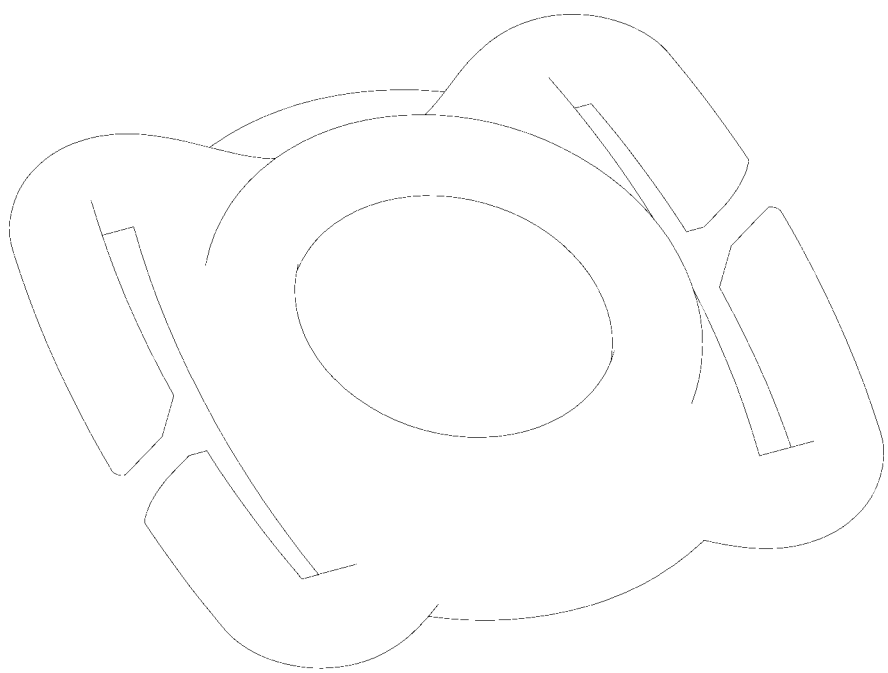
Figure 32A:
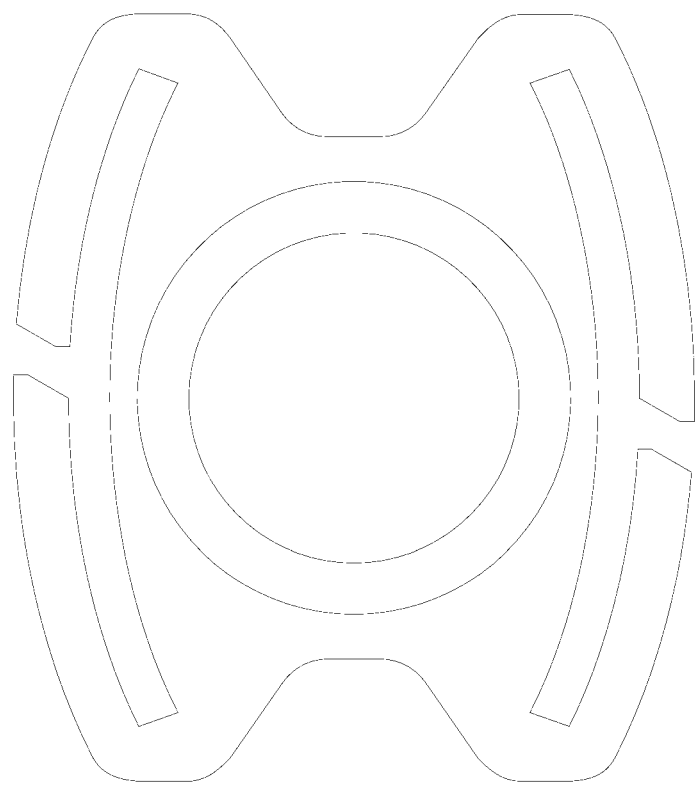
FIGS. 32A and 32B are bottom and top perspective view diagrams, respectively, illustrating an exemplary apparatus for use with a diabetes management device, in accordance with some embodiments of the present invention.
Figure 32B:
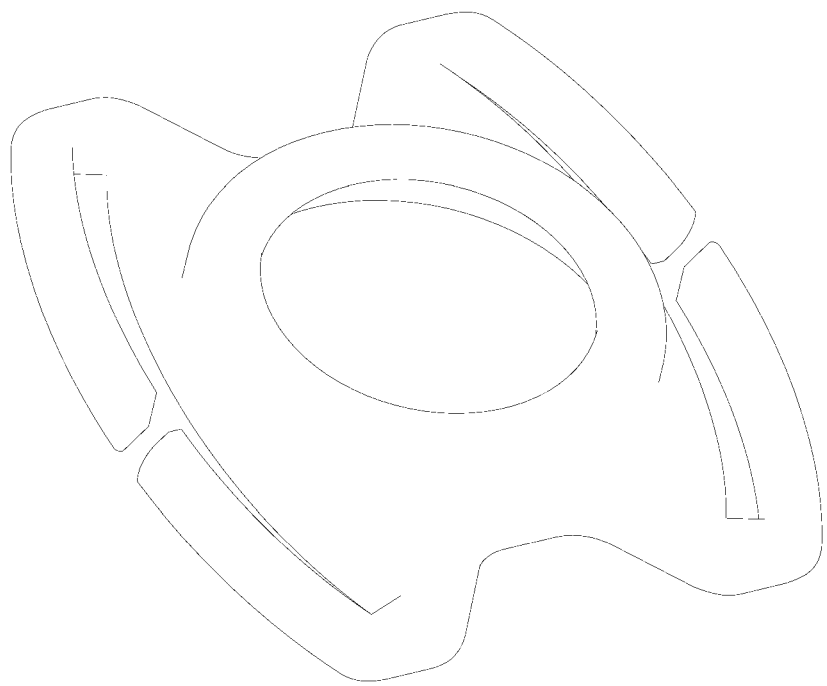
Figure 33A:
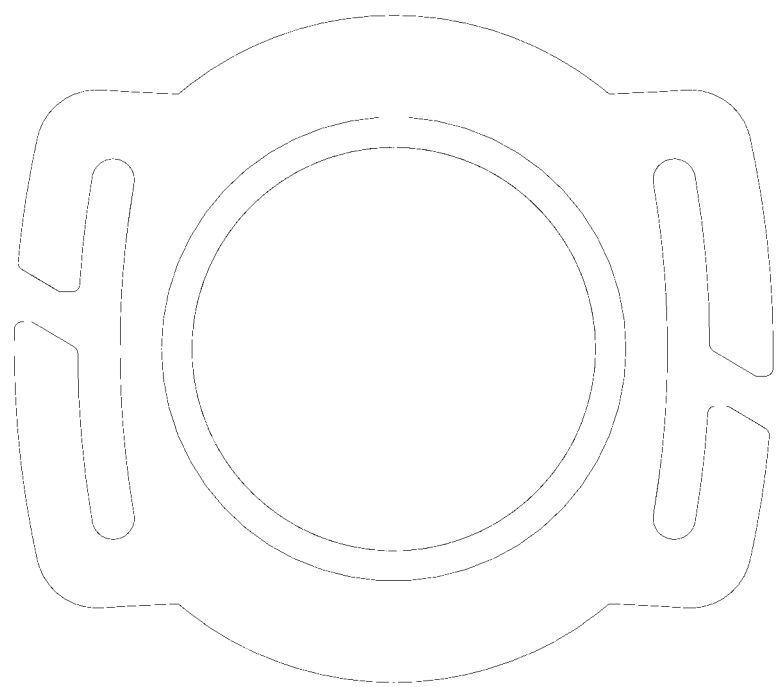
FIGS. 33A and 33B are bottom and top perspective view diagrams, respectively, illustrating an exemplary apparatus for use with a diabetes management device, in accordance with some embodiments of the present invention.
Figure 33B:
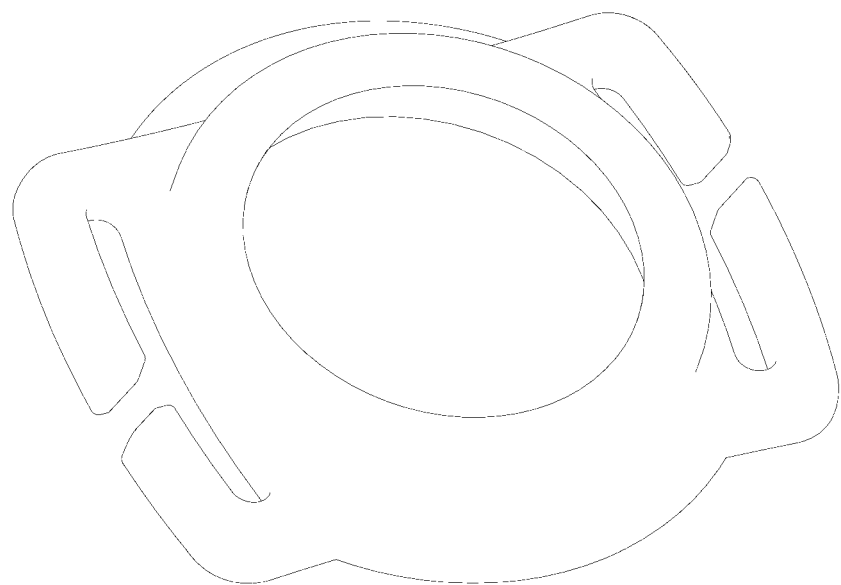
Figure 34:
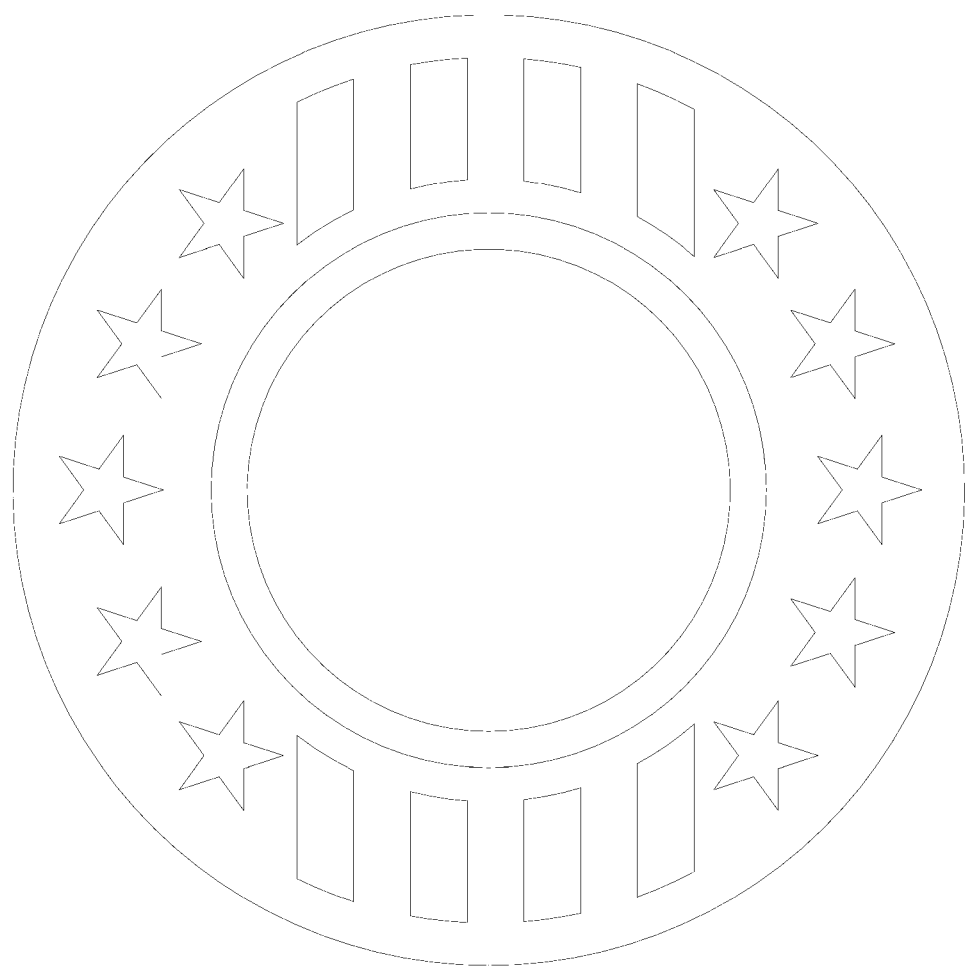
FIG. 34 is a bottom view diagram illustrating an exemplary apparatus for use with a diabetes management device, in accordance with some embodiments of the present invention.
Figure 35:
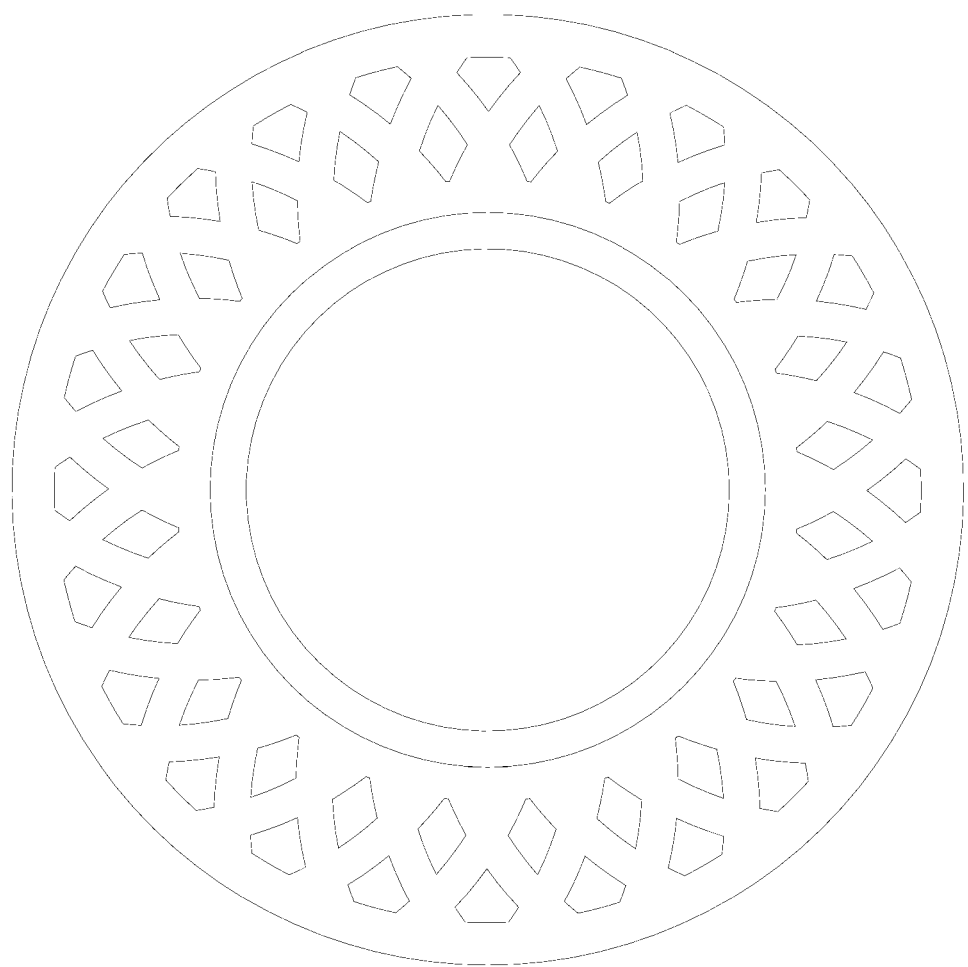
FIG. 35 is a bottom view diagram illustrating an exemplary apparatus for use with a diabetes management device, in accordance with some embodiments of the present invention.
Figure 36A:
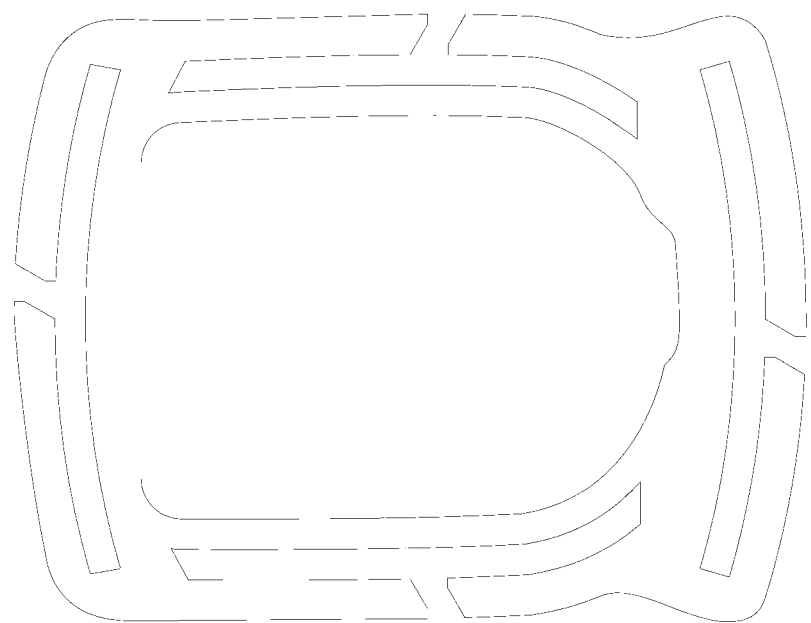
FIGS. 36A and 36B are bottom and top perspective view diagrams, respectively, illustrating an exemplary apparatus for use with a diabetes management device, in accordance with some embodiments of the present invention.
Figure 36B:
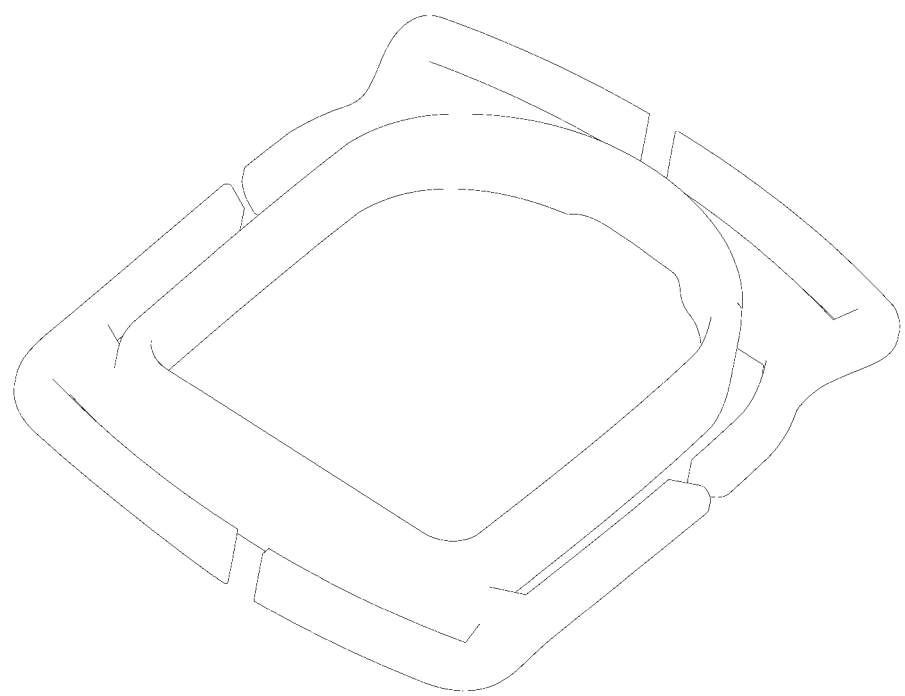
Figure 37A:
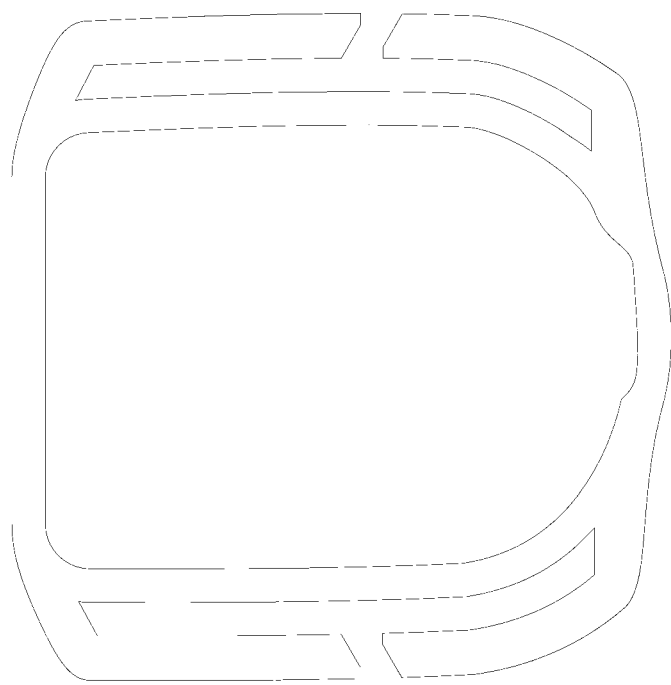
FIGS. 37A and 37B are bottom and top perspective view diagrams, respectively, illustrating an exemplary apparatus for use with a diabetes management device, in accordance with some embodiments of the present invention.
Figure 37B:
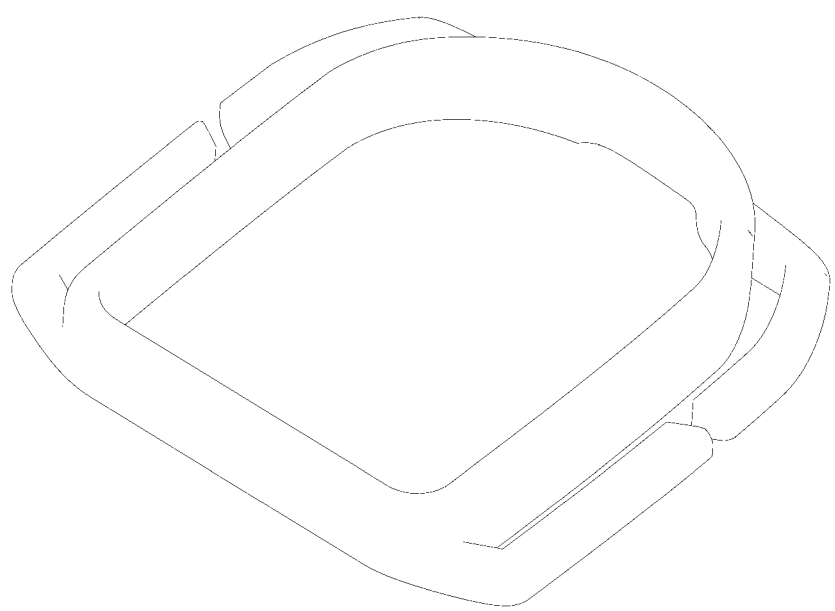
Figure 38:
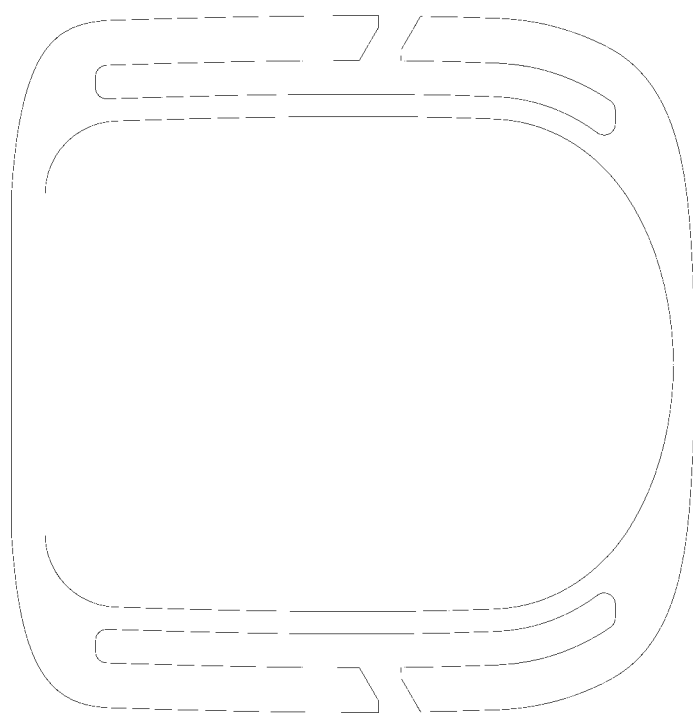
FIG. 38 is a top (bottom) view diagram illustrating an exemplary apparatus for use with a diabetes management device, in accordance with some embodiments of the present invention.

According to another implementation of the present invention, and with reference to FIGS. 19 and 20, a system may comprise a base 720, shell 730, diabetes management device 701, patch 750, and a band 740. As illustrated, patch 750 may be adhered to adhesion wall 738 of shell 730 (as well as a user's skin, not illustrated) and base 720 may be engaged with shell 730, with a bottom side of base 720 abutting a top side of patch 750. As further illustrated, when base 720 is engaged with shell 730, a plurality of tabs 729 (partially illustrated in FIG. 19) may be received and retained in corresponding grooves 737 of shell 730 (partially illustrated in FIGS. 19 and 20). Similar to previously described implementations, a first end of band 740 may be attached to a first arm 721C and second arm 722C (or, optionally, first arm 721A and second arm 722A) and a second end of band 740 may be attached to a first arm 721D and a second arm 722D (or, optionally, first arm 721B and second arm 722B), and with a portion of each end of band 740 being retained within corresponding band slots.

It is to be appreciated that a system for securing a diabetes management device may include a combination of a base, a shell, and a patch, or subcombinations thereof. In some embodiments, a system may comprise base and a shell. For example, referring briefly to FIG. 1, a system may include apparatus 10 (comprising base 20 and shell 30 as a unitary piece) which may be secured to a user by a band engaged with at least two of the band slots. Alternatively, and according to some embodiments, a system may include a shell and a patch. For example, with reference briefly to FIGS. 17 and 18, a system may include shell 730 and patch 750, where shell 730 may be secured to a user by patch 750 (and, thus, may not require the use of a band). Furthermore, and according to some embodiments, a system may include a base, a shell, and a patch. For example, and with reference briefly to FIGS. 19 and 20, a system may include base 720, shell 730 (as a separate piece from base 720), and patch 750, where shell 730 may be secured to a user by patch 750 and where base 720 may be secured by band 740 to optionally provide additional security to shell 730.

In addition to the various embodiments previously described herein, FIGS. 21-38 also illustrate several additional exemplary embodiments which are provided to demonstrate how the present invention may be modified for different applications. For example, FIGS. 21-38 illustrate several apparatuses, bases, and shells which may be configured for various diabetes management devices. More particularly, as can be appreciated from the exemplary illustrations, the base openings and/or shell openings may be shaped according to a particular shape of a diabetes management device for which an apparatus (or, separately, a shell) may be configured. Additionally, it is to be appreciated that, as illustrated in FIGS. 22-23, 26, 29-31, and 35-36, for example, some bases may comprise only two arm pairs and two band slots, which may limit how the base may be oriented on a user's skin. Furthermore, it is to be appreciated that a base and/or shell may be configured to accommodate certain features of a diabetes management device which may be specific to the particular diabetes management device. For example, with reference to FIG. 21, a shell 830 may comprise an access opening 839 which may be provided to allow a user to view or access a part of a diabetes management device when the diabetes management device is retained in shell 830.

It is to be understood that variations, modifications, and permutations of embodiments of the present invention may be made without departing from the scope thereof. It is also to be understood that the present invention is not limited by the specific embodiments, descriptions, or illustrations or combinations of either components or steps disclosed herein. Thus, although reference has been made to the accompanying figures, it is to be appreciated that these figures are exemplary and are not meant to limit the scope of the invention. In particular, it is to be appreciated that the present invention provides a plurality of means for attaching, securing, and/or protecting diabetes management devices which may not be limited by those embodiments and implementations described herein. Furthermore, it is to be appreciated that the present invention can be easily modified to accommodate other diabetes management devices for which the exemplary embodiments may not be specifically configured to accommodate. It is also to be understood that the features of the present invention may be used, in whole or in part, and in various combinations to achieve a common solution to problems inherent with using diabetes management devices as standalone devices or with conventional technology.

What is claimed is:

1. An apparatus for protecting and securing a diabetes management device, said diabetes management device having a side wall around its perimeter, a top wall, and a bottom wall, said apparatus comprising:
   a) a base comprising:
      i) a first pair of arms, each arm having an end;
      ii) a first band aperture between each end of each arm of said first pair of arms;
      iii) a first band slot adjacent to said first pair of arms and configured to receive a portion of a band; and
      iv) a base opening;
   b) a shell comprising:
      i) a retention opening having a shape similar to a shape of said bottom wall of said diabetes management device; and
      ii) a retention wall having an inner surface having a shape similar to a shape of said side wall of said diabetes management device;
   wherein said base is removably engaged with said shell, and
   wherein said base opening has a shape similar to a shape of an outer surface of said retention wall of said shell.

2. The apparatus of claim 1, wherein each end of each arm of said first pair of arms comprises a proximal surface and an adjacent distal surface and wherein said proximal surface and said distal surface are not coplanar.

3. The apparatus of claim 1, wherein said base further comprises:
   iv) a second pair of arms, each arm of said second pair of arms having an end;
   v) a second band aperture between each end of each arm of said second pair of arms; and
   vi) a second band slot adjacent to said second pair of arms and configured to receive a portion of said band;
   wherein each end of each arm of said second pair of arms comprises a proximal surface and an adjacent distal surface.

4. The apparatus of claim 3, wherein said first pair of arms is disposed at a first lateral side of said base and wherein said second pair of arms is disposed at a second lateral side of said base.

5. The apparatus of claim 3, wherein said proximal surface of said end of a first arm of said first pair of arms is about parallel to said proximal surface of said end of a first arm of said second pair of arms, and
   wherein said distal surface of said end of said first arm of said first pair of arms is about parallel to said distal surface of said end of said first arm of said second pair of arms.

6. The apparatus of claim 3, wherein said proximal surface of said end of a first arm of said first pair of arms is about parallel to said distal surface of said end of a first arm of said second pair of arms, and
   wherein said distal surface of said end of said first arm of said first pair of arms is about parallel to said proximal surface of said end of said first arm of said second pair of arms.

7. The apparatus of claim 3, wherein each band aperture is offset from a centerline of said base.

8. The apparatus of claim 7, wherein said first band aperture is offset from said centerline in a first direction and wherein said second band aperture is offset from said centerline in a second direction.

9. The apparatus of claim 1, wherein said shell further comprises:
  iii) at least one ridge formed on said inner surface of said retention wall.

10. The apparatus of claim 1, wherein said shell further comprises:
  iii) a lip adjacent to said retention wall and protruding therefrom.

11. The apparatus of claim 1, wherein said shell further comprises:
  iii) an enclosure wall at a top edge of said retention wall.

12. The apparatus of claim 11, wherein said enclosure wall of said shell extends radially inward from said retention wall.

13. The apparatus of claim 11, wherein said enclosure wall of said shell comprises an enclosure opening.

14. The apparatus of claim 11, wherein said enclosure wall of said shell comprises a rounded inner surface having a shape similar to a shape of said top wall of said diabetes management device to contour said diabetes management device when said diabetes management device is retained within said retention opening.

15. The apparatus of claim 1, wherein said retention wall of said shell is positioned within said base opening.

16. The apparatus of claim 1, wherein said first band aperture is medially disposed between each end of each arm of said first pair of arms near a lateral side of said base.

17. The apparatus of claim 1, wherein said base further comprises at least one tab formed on an inner surface of said base opening and wherein said shell further comprises at least one groove formed on an outer surface of said retention wall and configured to receive said at least one tab of said base.

18. The apparatus of claim 1, wherein said shell further comprises at least one tab formed on an outer surface of said retention wall and wherein said base further comprises at least one groove formed on an inner surface of said base opening, said at least one groove configured to receive said at least one tab of said shell.

19. A system for protecting and securing a diabetes management device, said diabetes management device having a side wall around its perimeter, a top wall, and a bottom wall,
  said system comprising an apparatus, a patch, and a band engaged with said apparatus,
  said patch comprising i) a patch opening, ii) an adhesive layer, iii) a plurality of liners overlaying said adhesive layer, and iv) a plurality of cutlines formed between said liners,
  said apparatus comprising:
  a) a base comprising:
    i) a first pair of arms and a second pair of arms, each arm having an end;
    ii) a first band aperture between each end of each arm of said first pair of arms and a second band aperture between each end of each arm of said second pair of arms;
    iii) a first band slot adjacent to said first pair of arms and a second band slot adjacent to said second pair of arms, each band slot configured to receive a portion of said band; and
    iv) a base opening;
  b) a shell comprising:
    i) a retention opening having a shape similar to a shape of said bottom wall of said diabetes management device; and
    ii) a retention wall having an inner surface having a shape similar to a shape of said side wall of said diabetes management device;
  wherein said base is removably engaged with said shell,
  wherein said base opening has a shape similar to a shape of an outer surface of said retention wall of said shell,
  wherein said patch opening of said patch has a shape similar to a shape of an outer surface of said retention wall of said shell,
  wherein a first portion of said band is positioned around said first pair of arms of said base,
  wherein a second portion of said band is positioned around said second pair of arms of said base, and
  wherein said diabetes management device is positioned within said retention opening of said shell.

20. The system of claim 19, wherein said shell further comprises an adhesion wall and wherein said patch is adapted to adhere to said adhesion wall.

21. The system of claim 19, wherein a first of said liners of said patch overlays a first area of said adhesive layer and wherein said first of said liners circumscribes said patch opening.

22. The system of claim 21, wherein a second and a third of said liners of said patch overlay a second area and a third area, respectively, of said adhesive layer,
  wherein said second area of said adhesive layer is disposed adjacent to each of said first area of said adhesive layer and a lateral edge of said patch, and
  wherein said third area of said adhesive layer is disposed adjacent to each of said second area of said adhesive layer and said lateral edge of said patch.

23. The system of claim 19, wherein said retention wall of said shell is positioned within said base opening.

* * * * *